US010710942B2

(12) United States Patent
Bafna et al.

(10) Patent No.: US 10,710,942 B2
(45) Date of Patent: Jul. 14, 2020

(54) METHOD OF CO-PROCESSING FLUIDIZED CATALYTIC CRACKING NAPHTHA AND PYROLYSIS GASOLINE

(71) Applicant: SABIC GLOBAL TECHNOLOGIES B.V., Bergen op Zoom (NL)

(72) Inventors: Sheetal Bafna, Sugar Land, TX (US); Sanjeev Deshpande, Sugar Land, TX (US); Michael Huckman, Sugar Land, TX (US); Scott Stevenson, Sugar Land, TX (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/303,847

(22) PCT Filed: May 12, 2017

(86) PCT No.: PCT/US2017/032374
§ 371 (c)(1),
(2) Date: Nov. 21, 2018

(87) PCT Pub. No.: WO2017/205083
PCT Pub. Date: Nov. 30, 2017

(65) Prior Publication Data
US 2019/0359541 A1 Nov. 28, 2019

Related U.S. Application Data

(60) Provisional application No. 62/339,991, filed on May 23, 2016.

(51) Int. Cl.
C07C 4/04 (2006.01)
C07C 4/14 (2006.01)
(Continued)

(52) U.S. Cl.
CPC .............. C07C 4/04 (2013.01); C07C 4/14 (2013.01); C07C 5/2702 (2013.01); C07C 9/16 (2013.01);
(Continued)

(58) Field of Classification Search
CPC ............ C07C 4/04; C07C 5/2702; C07C 4/14
(Continued)

(56) References Cited

U.S. PATENT DOCUMENTS 7,270,739 B2  9/2007  Chen et al.
7,301,063 B2  11/2007 Choi et al.
(Continued)

FOREIGN PATENT DOCUMENTS

CN    101492608 A    7/2009
GB      1301019      12/1972
WO    2017205083     11/2017

OTHER PUBLICATIONS

Magyar, S., et al., "Investigation of the desulfurization of FCC gasoline and pyrolysis gasoline/FCC gasoline mixture over precious metals/support catalyst," 230th ACS National Meeting, 2005, abstract, 2 pages.
(Continued)

Primary Examiner — Thuan D Dang
(74) Attorney, Agent, or Firm — Norton Rose Fulbright US LLP

(57) ABSTRACT

An integrated process for forming a combined feedstock stream comprising catalytically cracking a first hydrocarbon feedstock to form a full range cracked full naphtha stream and a first light olefins stream, steam cracking a second hydrocarbon feedstock to form a pyrolysis gasoline stream and a second light olefins stream mixing at least a portion of each of the full range cracked naphtha stream and the pyrolysis gasoline stream to form a combined stream, hydro-
(Continued)

processing the combined stream to form a hydro-processed combined stream splitting the hydro-processed combined stream into a $C_5/C_6$ stream, and a first aromatic rich stream, splitting the first aromatic rich stream into a second aromatic rich stream and a heavy oil stream.

7 Claims, 5 Drawing Sheets

(51) Int. Cl.
    *C07C 5/27*       (2006.01)
    *C07C 9/16*       (2006.01)
    *C07C 11/04*     (2006.01)
    *C07C 11/06*     (2006.01)
    *C07C 15/04*     (2006.01)
    *C07C 15/06*     (2006.01)
    *C07C 15/08*     (2006.01)

(52) U.S. Cl.
    CPC .............. *C07C 11/04* (2013.01); *C07C 11/06* (2013.01); *C07C 15/04* (2013.01); *C07C 15/06* (2013.01); *C07C 15/08* (2013.01)

(58) Field of Classification Search
    USPC ................ 585/648, 651, 652, 653, 250, 258
    See application file for complete search history.

(56) References Cited

U.S. PATENT DOCUMENTS

| | | |
|---|---|---|
| 7,341,657 B2 | 3/2008 | Li et al. |
| 8,450,544 B2 | 5/2013 | Tsao et al. |
| 8,808,533 B2 | 8/2014 | Nocca et al. |
| 8,940,950 B2 | 1/2015 | Enrich et al. |
| 2012/0149958 A1 | 6/2012 | Enrich et al. |
| 2015/0141706 A1 | 5/2015 | Choi et al. |
| 2016/0090335 A1 | 3/2016 | Luebke et al. |

OTHER PUBLICATIONS

Foreign communication from a priority application—International Search Report and Written Opinion, PCT/US2017/032374, dated Sep. 19, 2017, 15 pages.
Filing Receipt and Specification of U.S. Appl. No. 62/339,991, filed May 23, 2016, entitled "A Method of Co-Processing Fluidized Catalytic Cracking Naphtha and Pyrolysis Gasoline," 39 pages.
Foreign communication from a related priority application—International Preliminary Report on Patentability, PCT/US2017/032374, Nov. 27, 2018, 11 pages.

METHOD OF CO-PROCESSING FLUIDIZED CATALYTIC CRACKING NAPHTHA AND PYROLYSIS GASOLINE

CROSS REFERENCE TO RELATED APPLICATIONS

This application is a filing under 35 U.S.C. 371 of International Application No. PCT/US2017/032374 filed May 12, 2017, entitled "A Method of Co-Processing Fluidized Catalytic Cracking Naphtha and Pyrolysis Gasoline," which claims the benefit of U.S. Provisional Application No. 62/339,991 filed May 23, 2016, entitled "A Method of Co-Processing Fluidized Catalytic Cracking Naphtha and Pyrolysis Gasoline," which applications are incorporated by reference herein in their entirety.

BACKGROUND OF THE INVENTION

Technical Field

An integrated process for forming and hydro-processing a combined feedstock stream comprising a full range cracked naphtha stream and a pyrolysis gasoline stream to increase olefins/aromatics production.

Description of the Related Art

Traditionally, petrochemical hydrocarbon streams from FCC and steam cracking units are hydro-processed separately to produce aromatic and/or olefinic products. The high mono olefin content of FCC hydrocarbon streams is hydro-processed in a single stage to produce high octane value olefinic/naphthenic materials with low sulfur, nitrogen and/or metal content. As a result, hydro-processed FCC naphtha streams are traditionally used as important gasoline blending components. Both cracking methods produce aromatically-rich streams for the production of valuable aromatics/polyaromatics such as benzene ($C_6$), toluene ($C_7$), and xylenes ($C_8$). When coupled with an ever increasing worldwide demand for olefins and aromatics, the petrochemical industry is constantly seeking more efficient industrial processes for meeting demands.

Attempts to improve processing methods include mixing separately hydro-processed naphtha streams into a singular hydrocarbon stream to accommodate different feedstocks, [see, Nocca et al., U.S. Pat. No. 8,808,533B2, incorporated herein by reference in its entirety] and/or subjecting a combined stream to a series of downstream refining procedures to produce desired products [see, Choi et. al, U.S. Pat. No. 7,107,063B2, incorporated herein by reference in its entirety]. Unfortunately, these processes often lead to combined streams with lower aromatic and/or olefin contents, and limited potential for producing multiple product lines. Additionally, to date no combined process has found a way to mitigate the higher operational costs associated with running multiple hydro-processing units.

In view of the forgoing, the objective of the present disclosure is to provide a method for increasing production of olefin and aromatic hydrocarbon streams by co-processing different hydrocarbon feedstocks.

BRIEF SUMMARY OF THE INVENTION

According to a first aspect, the present disclosure relates to an integrated process for forming a combined feedstock stream comprising a pyrolysis gasoline stream and a full range cracked naphtha stream to produce a plurality of olefin streams and a plurality of aromatic hydrocarbon streams, comprising, i) catalytically cracking a first hydrocarbon feedstock to form a full range cracked naphtha stream and a first light olefins stream wherein the first light olefins stream comprises ethylene, propylene, butadiene and/or any combination thereof, ii) steam cracking a second hydrocarbon feedstock to form a heavy pyrolysis oil stream, a pyrolysis gasoline stream, and a second light olefins stream wherein the second light olefin stream comprises ethylene, propylene, butadiene and/or any combination thereof, iii) mixing at least a portion of each of the full range cracked naphtha stream and the pyrolysis gasoline stream to form a combined stream, iv) hydro-processing the combined stream to form a hydro-processed combined stream, and a light pyrolysis oil stream and, v) splitting the hydro-processed combined stream into a) a $C_5/C_6$ stream and b) a first aromatic rich stream comprising $C_6$, $C_7$, $C_8$, $C_9$ molecules and/or any combination thereof, vi) splitting the first aromatic rich stream into a) a second aromatic rich stream and b) a heavy oil stream.

In one embodiment, the hydro-processing comprises a) hydrogenating the combined stream with a first hydro-processing catalyst to convert one or more diolefins present in the combined stream into one or more mono-olefins b) saturating the hydrogenated combined stream with a second hydro-processing catalyst to convert mono-olefins into paraffins and c) removing one or more components comprising nitrogen, sulfur, metals and/or any combination thereof from the combined stream to form the hydro-processed combined stream.

In one embodiment, the full range cracked naphtha stream comprises by weight a) 5%-40% mono-olefins b) 10%-20% paraffins c) 30%-45% aromatics/polyaromatics, and/or any combination thereof.

In one embodiment, the pyrolysis gasoline stream comprises by weight a) 5%-10% mono-olefins b) 10%-20% paraffins c) 15%-25% diolefins d) 30%-55% aromatics/polyaromatics, and or any combination thereof.

In one embodiment, the combined stream comprises by weight a) 10%-20% mono-olefins b) 10%-20% paraffins c) 15%-20% diolefins d) 35%-50% aromatics/polyaromatics, and or any combination thereof.

In one embodiment, up to 99% of the diolefins by weight are hydrogenated to form mono-olefins during the hydro-processing.

In one embodiment, at least 98% of the mono-olefins by weight are saturated during the hydro-processing to form paraffins.

In one embodiment, the hydro-processing forms a hydro-processed combined stream having a sulfur content of less than 2 ppm.

In one embodiment, the process further comprises isomerizing the $C_5/C_6$ stream to form an isomerized stream.

In one embodiment, the process further comprises steam cracking the isomerized stream.

In one embodiment, the process further comprises extracting the benzene, the toluene, the xylenes, and/or any combination thereof, from the second aromatic rich stream to form a raffinate stream and a third aromatic rich stream.

In one embodiment, the process wherein the third aromatic rich stream comprises: benzene, toluene, xylenes, and/or any combination thereof.

In one embodiment, the process further comprises steam cracking the raffinate stream to form a second olefin stream.

In one embodiment, the $C_5/C_6$ stream comprises compounds having less than or equal to 6 carbon atoms.

In one embodiment, the heavy oil stream comprises $C_{9+}$ hydrocarbons.

In one embodiment, the first aromatic rich stream comprises by weight an aromatic/polyaromatic content of at least 15%.

In one embodiment, the heavy pyrolysis oil stream and the light pyrolysis oil stream are delivered to a fuel oil pool.

In one embodiment, the $C_{9+}$ hydrocarbons molecular structure comprises at least nine carbon atoms.

In one embodiment, the third aromatic rich stream is optionally sent to a dealkylating unit to produce a benzene rich stream.

In one embodiment, the benzene rich stream comprises by weight at least 40% benzene.

According to a second aspect the present disclosure relates to an integrated process for increasing olefin production from a combined feedstock stream composing a pyrolysis gasoline stream and a full range cracked naphtha stream comprising, i) catalytically cracking a first hydrocarbon feedstock to form a full range cracked naphtha stream and a first light olefins stream wherein the first light olefins stream comprises ethylene, propylene, butadiene and/or any combination thereof, ii) steam cracking a second hydrocarbon feedstock to form a heavy pyrolysis oil stream, a pyrolysis gasoline stream, and a second light olefins stream wherein the second light olefins stream comprises ethylene, propylene, butadiene and/or any combination thereof, iii) mixing at least a portion of each of the full range cracked naphtha stream and the pyrolysis gasoline stream to form a combined stream, iv) hydro-processing the combined stream to form a hydro-processed combined stream, and a light pyrolysis oil stream, v) splitting the hydro-processed combined stream in a first splitter into a) a $C_5/C_6$ stream and b) a first aromatic rich stream comprising $C_6$, $C_7$, $C_8$, $C_9$ molecules and/or any combination thereof, vi) saturating at least a portion of the first aromatic rich stream, at least a portion of the light pyrolysis oil stream and/or both to produce a first naphthene stream.

In one embodiment, the hydro-processing comprises a) hydrogenating the combined stream with a first hydro-processing catalyst to convert one or more diolefins present in the combined stream into one or more mono-olefins b) saturating the hydrogenated combined stream with a second hydro-processing catalyst to convert mono-olefins into paraffins and c) removing one or more components comprising nitrogen, sulfur, metals and/or any combination thereof from the combined stream to form the hydro-processed combined stream.

In one embodiment, the full range cracked naphtha stream comprises by weight a) 5%40% mono-olefins b) 10%-20% paraffins c) 30%-45% aromatics/polyaromatics, and/or any combination thereof.

In one embodiment, the pyrolysis gasoline stream comprises by weight a) 5%-10% mono-olefins b) 10%-20% paraffins c) 15%-25% diolefins d) 30%-55% aromatics/polyaromatics, and or any combination thereof.

In one embodiment, the combined stream comprises by weight a) 10%-20% mono-olefins b) 10%-20% paraffins c) 15%-20% diolefins d) 35%-50% aromatics/polyaromatics, and or any combination thereof.

In one embodiment, up to 99% of the diolefins by weight are hydrogenated to form mono-olefins during the hydro-processing.

In one embodiment, at least 98% of the mono-olefins by weight are saturated during the hydro-processing to form paraffins.

In one embodiment, the hydro-processing forms a hydro-processed combined stream having a sulfur content of less than 2 ppm.

In one embodiment, the process further comprises isomerizing the $C_5/C_6$ stream to form an isomerized stream.

In one embodiment, saturating the first aromatic rich stream converts at least 90% of the aromatic/polyaromatic content into naphthenes.

In one embodiment, the process further comprises reducing a dicyclopentadiene content of the light pyrolysis oil stream and/or the first aromatic rich stream prior to the saturating.

In one embodiment, the process further comprises steam cracking the first naphthene stream.

In one embodiment, the $C_5/C_6$ stream comprises compounds having less than or equal to 6 carbon atoms.

In one embodiment, the first aromatic rich stream comprises by weight an aromatic/polyaromatic content of at least 15%.

According to a third aspect, the present disclosure relates to an integrated process for increasing aromatic production with minimal olefin production loss using a combined feedstock stream comprising a pyrolysis gasoline stream and a full range cracked naphtha stream comprising, i) catalytically cracking a first hydrocarbon feedstock to form a full range cracked naphtha stream and a first light olefin stream wherein the first light olefins stream comprises ethylene, propylene, butadiene and/or any combination thereof, ii) steam cracking a second hydrocarbon feedstock to form a heavy pyrolysis oil stream, a pyrolysis gasoline stream, and a second light olefins stream wherein the second light olefin stream comprises ethylene, propylene, butadiene and/or any combination thereof, iii) mixing at least a portion of each of the full range cracked naphtha stream and the pyrolysis gasoline stream to form a combined stream, iv) hydro-processing the combined stream to form a hydro-processed combined stream and a light pyrolysis oil stream, v) splitting the hydro-processed combined stream in a first splitter into a) a $C_5/C_6$ stream and b) a first aromatic rich stream comprising $C_6$, $C_7$, $C_8$, $C_{9+}$ molecules and/or any combination thereof, vi) splitting the first aromatic rich stream in a second splitter into a) a second aromatic rich stream and b) a heavy oil stream, vii) extracting the benzene, the toluene, the xylenes, and/or any combination thereof from at least a portion of the second aromatic rich stream to form a raffinate stream and a third aromatic rich stream comprising benzene, toluene, xylenes, and/or any combination thereof, viii) saturating at least a portion of the third aromatic rich stream, optionally a portion of light pyrolysis oil stream, and at least a portion of the heavy oil stream to produce a second naphthene stream, ix) dealkylating a portion of the third aromatic rich stream to produce a benzene rich stream.

In one embodiment, the hydro-processing comprises a) hydrogenating the combined stream with a first hydro-processing catalyst to convert one or more diolefins present in the combined stream into one or more mono-olefins b) saturating the hydrogenated combined stream with a second hydro-processing catalyst to convert mono-olefins into paraffins and c) removing one or more components comprising nitrogen, sulfur, metals and/or any combination thereof from the combined stream to form the hydro-processed combined stream.

In one embodiment, the full range cracked naphtha stream comprises by weight a) 5%40% mono-olefins b) 10%-20% paraffins c) 30%-45% aromatics/polyaromatics, and/or any combination thereof.

In one embodiment, the pyrolysis gasoline stream comprises by weight a) 5%-10% mono-olefins b) 10%-20% paraffins c) 15%-25% diolefins d) 30%-55% aromatics/polyaromatics, and or any combination thereof.

In one embodiment, the combined stream comprises by weight a) 10%-20% mono-olefins b) 10%-20% paraffins c) 15%-20% diolefins d) 35%-50% aromatics/polyaromatics, and or any combination thereof.

In one embodiment, up to 99% of the diolefins by weight are hydrogenated to form mono-olefins during the hydro-processing.

In one embodiment, at least 98% of the mono-olefins by weight are saturated during the hydro-processing to form paraffins.

In one embodiment, the hydro-processing forms a hydro-processed combined stream having a sulfur content of less than 2 ppm.

In one embodiment, the process further comprises isomerizing the $C_5/C_6$ stream to form an isomerized stream.

In one embodiment, the process further comprises steam cracking the isomerized stream to produce a second olefin stream.

In one embodiment, the process further comprises steam cracking the raffinate stream to form a second olefin stream.

In one embodiment, at least 90% of the aromatic/polyaromatic content of at least a portion of the second aromatic rich stream, at least a portion of the heavy oil stream, at least a portion of light pyrolysis oil stream and/or combination thereof is converted into naphthenes during the saturating.

In one embodiment, the process further comprises reducing a dicyclopentadiene content of the first aromatic rich stream, the heavy oil stream, and/or the light pyrolysis oil stream prior to the saturating.

In one embodiment, the process further comprises steam cracking the second naphthene stream.

In one embodiment, the $C_5/C_6$ stream comprises compounds having less than or equal to 6 carbon atoms.

In one embodiment, the heavy oil stream comprises $C_{9+}$ hydrocarbons.

In one embodiment, the second aromatic rich stream comprises by weight an aromatic/polyaromatic content of at least 15%.

In one embodiment, the $C_{9+}$ hydrocarbons molecular structure comprises at least nine carbon atoms.

In one embodiment, the benzene rich stream comprises by weight at least 40% benzene.

In one embodiment, the total benzene production by weight increases at least 25% when compared to the total benzene production from a process not using a combined feedstock, and dealkylating.

DETAILED DESCRIPTION OF THE EMBODIMENTS

Figure 1:
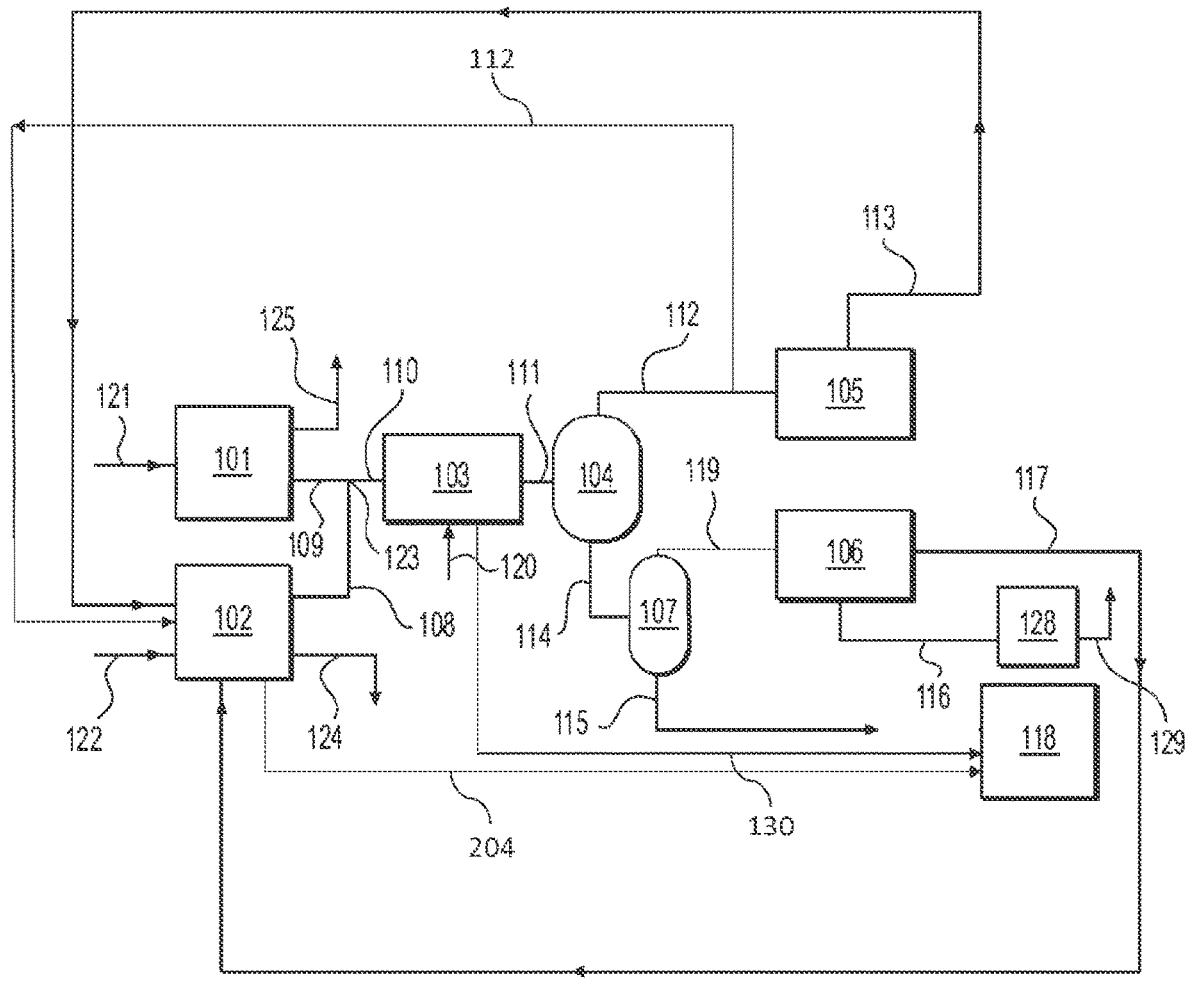
FIG. 1 is a schematic flow diagram illustrating the process steps of one embodiment of the invention and products produced therefrom.

Referring now to FIG. 1 where an integrated process for producing a plurality of olefin streams and aromatic rich streams using a combined feedstock stream is illustrated. A first hydrocarbon feedstock is fed through a line (121) to a catalytic cracking unit (e.g., a fluid catalytic cracking unit (101)) to produce a full range cracked naphtha stream (109) and a first light olefins stream (125) wherein the first light olefins stream comprises ethylene, propylene, butadiene and/or any combination thereof. A second hydrocarbon feedstock is fed through a second line (122) to a steam cracking unit (102) to produce a pyrolysis gasoline stream (108), a second light olefins stream (124), and a heavy pyrolysis oil stream (204) wherein the second light olefins stream comprises ethylene, propylene, butadiene and/or any combination thereof. The resulting full range cracked naphtha stream (109) and the pyrolysis gasoline stream (108) are combined and mixed (123) to form a combined stream (110). The combined stream (110) and hydrogen gas (120) are fed to a hydro-processing unit (103) to produce a hydro-processed combined stream (111) and a light pyrolysis oil stream (130). The hydro-processed combined stream (111) undergoes splitting in a first splitter (104) to form a $C_5/C_6$ stream (112) and a first aromatic rich stream (114). The first aromatic rich stream (114) is split in a second splitter (107) to form a second aromatic rich stream (119) and a heavy oil stream (115). The $C_5/C_6$ stream (112) is transported to the steam cracking unit (102) as feedstock for forming the second light olefin stream. Optionally, a fraction of the $C_5/C_6$ stream can be passed to an isomerization unit (105) to form an isomerized stream (113) which is then transported to the steam cracking unit (102) as feedstock for forming the second light olefins stream (124). The second aromatic rich stream (119) is passed to an extracting unit (106) to form a third aromatic rich stream (116) containing benzene, toluene, xylenes and/or any combination thereof, and a raffinate stream (117). Optionally, a portion of the third aromatic rich stream (116) is passed to a dealkylating unit (128) to form a benzene rich stream (129). The raffinate stream (117) is fed to the steam cracking unit (102) as additional feedstock for forming the second light olefin stream (124). The light pyrolysis oil stream (130) and the heavy pyrolysis oil stream (204) are delivered to a fuel oil pool (118).

Figure 2:
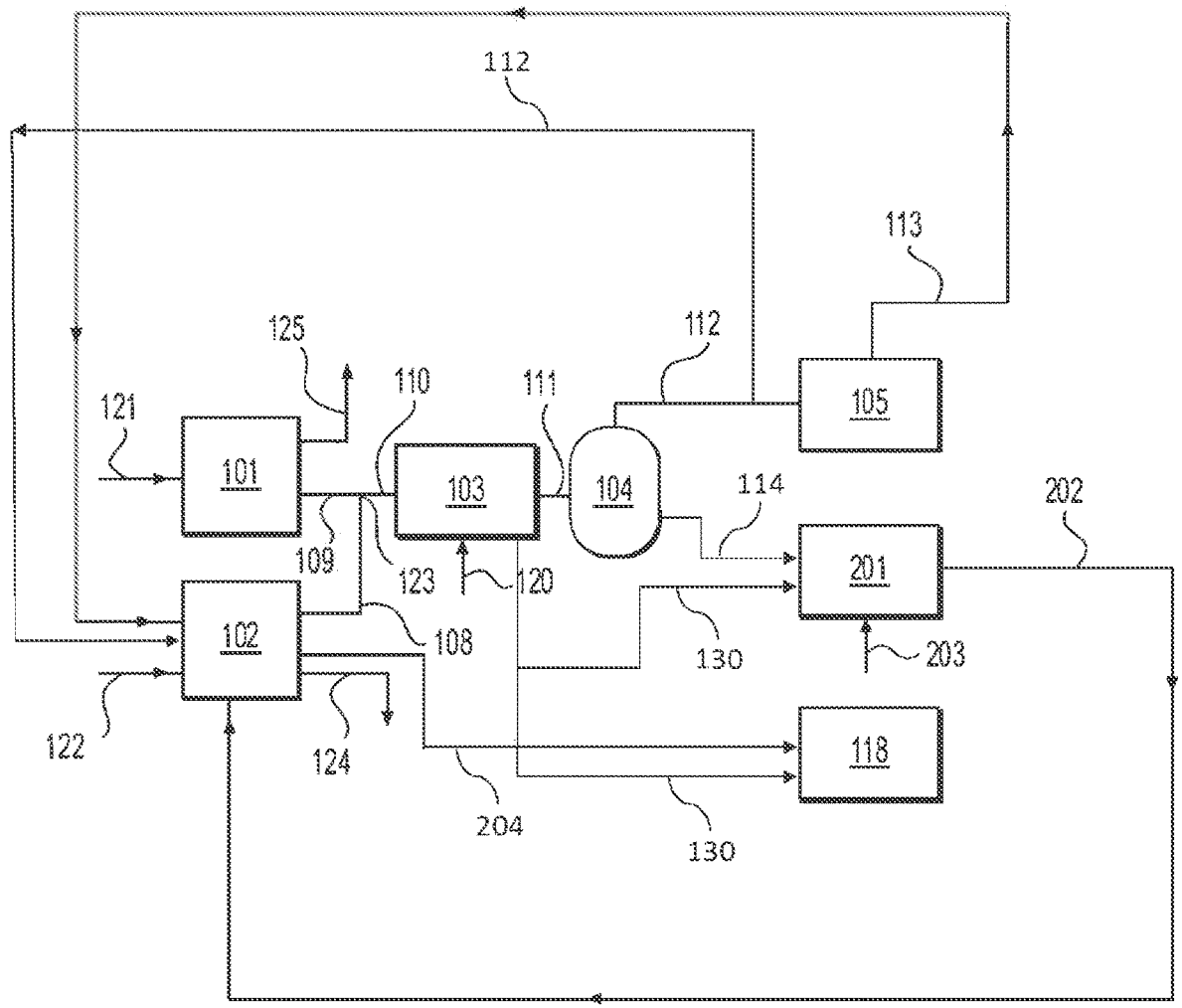
FIG. 2 is a schematic flow diagram illustrating the process steps of an alternative embodiment of the invention and products produced therefrom.

Referring now to FIG. 2 where an integrated process for increasing olefin production using a combined feedstock stream is illustrated. A first hydrocarbon feedstock is fed through a line (121) to a catalytic cracking unit (e.g., a fluid catalytic cracking unit (101)) to produce a full range cracked naphtha stream (109) and a first light olefins stream (125) wherein the first light olefins stream comprises ethylene, propylene, butadiene and/or any combination thereof. A second hydrocarbon feedstock is fed through a second line (122) to a steam cracking unit (102) to produce a pyrolysis gasoline stream (108), a heavy pyrolysis oil stream (204), and a second light olefins stream (124), wherein the second light olefins stream (124) comprises ethylene, propylene, butadiene and/or any combination thereof. The resulting full range cracked naphtha stream (109) from the catalytic cracking unit (101) and the pyrolysis gasoline stream (108) from the steam cracking unit (102) are combined (123) to form a combined stream (110). The combined stream (110)

and hydrogen gas (120) are fed to a hydro-processing unit (103) to form a hydro-processed combined stream (111), and a light pyrolysis oil stream (130). The hydro-processed combined stream (111) undergoes splitting in a first splitter (104) to yield a $C_5/C_6$ stream (112), and a first aromatic rich stream (114). The $C_5/C_6$ stream (112) is transported to the steam cracking unit (102) as feedstock for forming the second light olefin stream. Optionally, a fraction of the $C_5/C_6$ stream can be passed to an isomerization unit (105) to form an isomerized stream (113), which is then transported to the steam cracking unit (102) as feedstock for forming the second light olefins stream (124). The first aromatic rich stream (114) is fed to a saturating unit (201) to hydrogenate aromatic components and form a first naphthene stream (202) in the presence of hydrogen (203). The first naphthene stream (202) is fed to the steam cracking unit (102) as feedstock for forming the second light olefins stream (124). The light pyrolysis oil stream (130) and the heavy pyrolysis oil stream (204) are delivered to the fuel oil pool (118). A portion of the light pyrolysis oil stream (130) is optionally delivered to the saturating unit (201).

Figure 3:
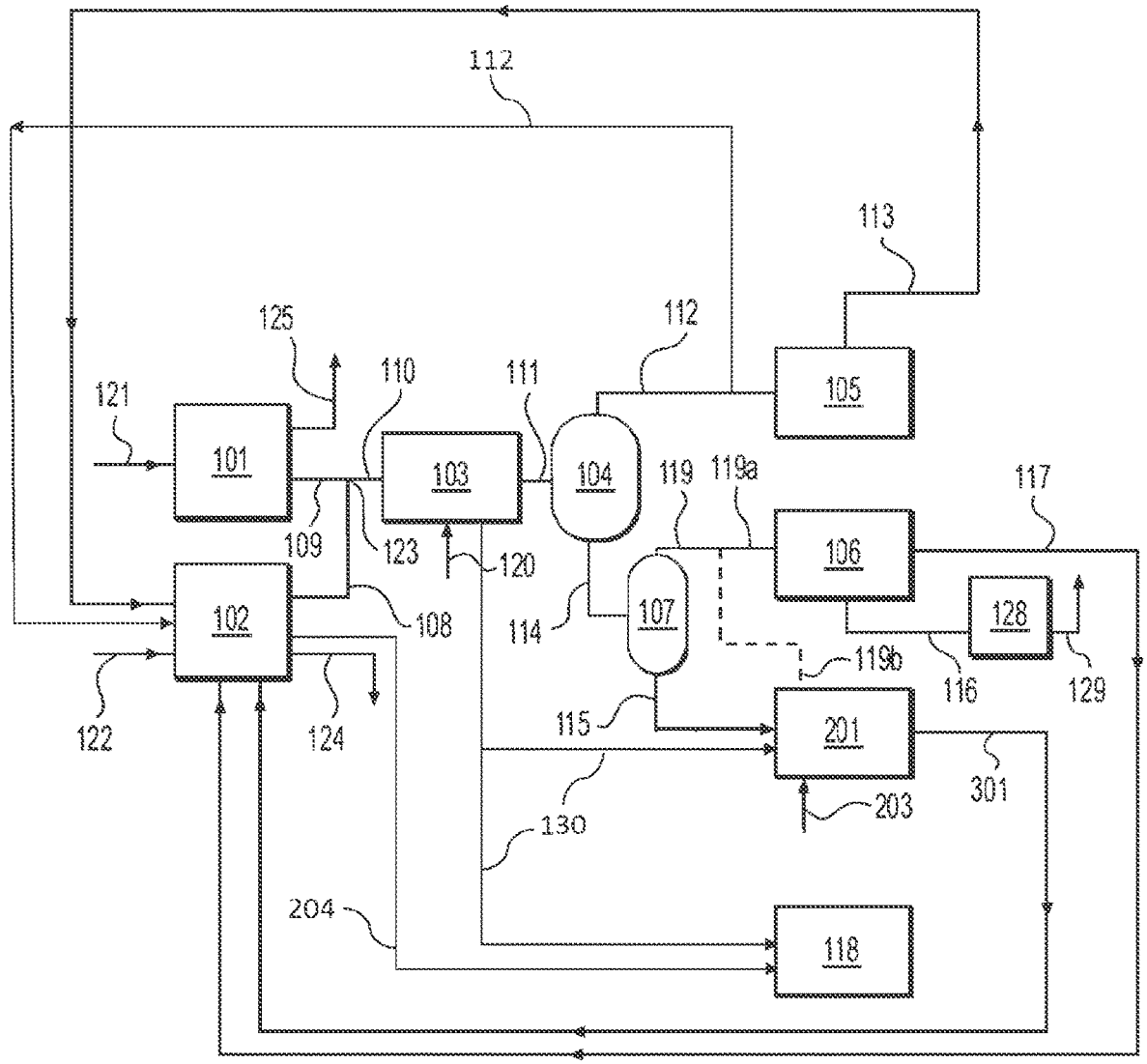
FIG. 3 is a schematic flow diagram illustrating the process steps of a second alternative embodiment of the invention and products produced therefrom.

Referring now to FIG. 3 where an integrated process for increasing aromatic production using a combined feedstock stream is illustrated. A first hydrocarbon feedstock is fed through a line (121) to a catalytic cracking unit (e.g., a fluid catalytic cracking unit (101)) to produce a full range cracked naphtha stream (109) and a first light olefins stream (125) wherein the first light olefins stream comprises ethylene, propylene, butadiene and/or any combination thereof. A second hydrocarbon feedstock is fed through a second line (122) to a steam cracking unit (102) to produce a pyrolysis gasoline stream (108) a heavy pyrolysis oil stream (204), and a second light olefins stream (124) wherein the second light olefin stream (124) comprises ethylene, propylene, butadiene and/or any combination thereof. The resulting full range cracked naphtha stream (109) and the pyrolysis gasoline stream (108) are combined (123) to form a combined stream (110). The combined stream (110) and hydrogen gas (120) are fed to a hydro-processing unit (103) to produce a hydro-processed combined stream (111), and a light pyrolysis oil stream (130). The hydro-processed combined stream (111) undergoes a splitting in a first splitter (104) to yield a $C_5/C_6$ stream (112) and a first aromatic rich stream (114). The $C_5/C_6$ stream (112) is transported to the steam cracking unit (102) as feedstock for forming the second light olefin stream. Optionally, a fraction of the $C_5/C_6$ stream can be passed to an isomerization unit (105) to form an isomerized stream (113), which is then transported to the steam cracking unit (102) as feedstock for forming the second light olefins stream (124). The first aromatic rich stream (114) is fed to a second splitter (107) to form a second aromatic rich stream (119) and a heavy oil stream (115). The second aromatic rich stream (119) is passed to an extracting unit (106) to form a third aromatic rich stream (116) containing benzene, toluene, xylenes and/or any combination thereof, and a raffinate stream (117). Optionally, a portion of the third aromatic rich stream (116) is passed to a dealkylating unit (128) to form a benzene rich stream (129). Optionally, in the presence of hydrogen gas (203), which is fed to a saturating unit (201), at least a portion of the second aromatic rich stream (119b), the heavy oil stream (115) and/or any combination thereof is passed to a saturating unit (201). The saturating unit hydrogenates aromatic components within the portion of second aromatic rich stream (119b), the heavy oil stream (115) and/or any combination to form a second naphthene stream (301). The isomerized stream (113) is transported to the steam cracking unit (102) for use as feedstock for forming the second light olefins stream (124), the raffinate stream (117) is fed to the steam cracking unit (102) as feedstock for forming the second light olefins stream (124) and the second naphthene stream (301) is fed to the steam cracking unit (102) as feedstock for forming the second light olefins stream (124). The light pyrolysis oil stream (130) and the heavy pyrolysis oil stream (204) are delivered to the fuel oil pool (118). A portion of the light pyrolysis oil stream (130) is optionally delivered to the saturating unit (201).

Figure 4:
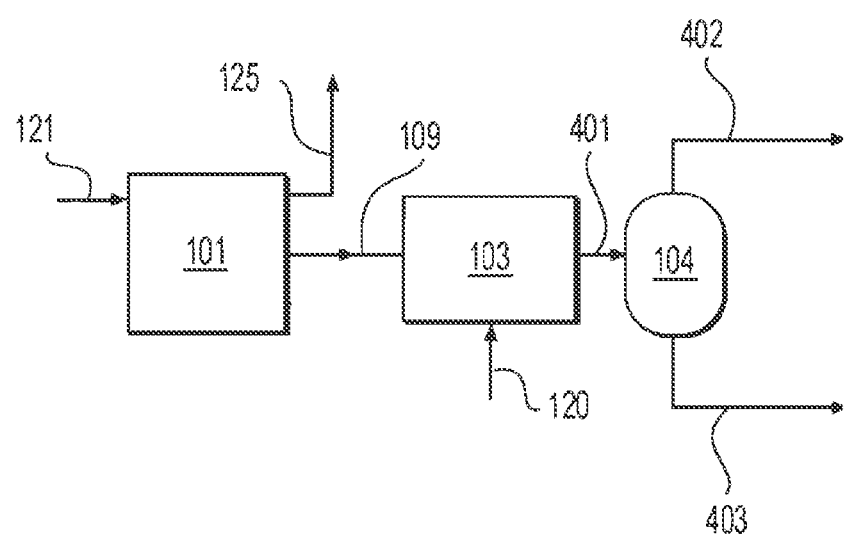
FIG. 4 is a schematic flow diagram illustrating the process steps of a non-integrated base catalytic cracking process and products produced therefrom.

Referring now to FIG. 4 where a non-integrated catalytic cracking process is illustrated. A first hydrocarbon feedstock passes through a line (121) into a catalytic cracking unit (101) to form a full range cracked naphtha stream (109), a first light olefins stream (125). The full range cracked naphtha stream (109) is fed to a hydro-processing unit (103), in the presence of hydrogen gas (120) to produce a hydro-processed naphtha stream (401). The hydro-processed naphtha stream (401) undergoes a splitting (104) to yield a $C_5/C_6$ naphtha stream (402) and a first aromatic rich stream (403). In one embodiment, the $C_5/C_6$ naphtha stream (402) and the first aromatic rich stream (403) can optionally be directed to the steam cracking unit.

Figure 5:
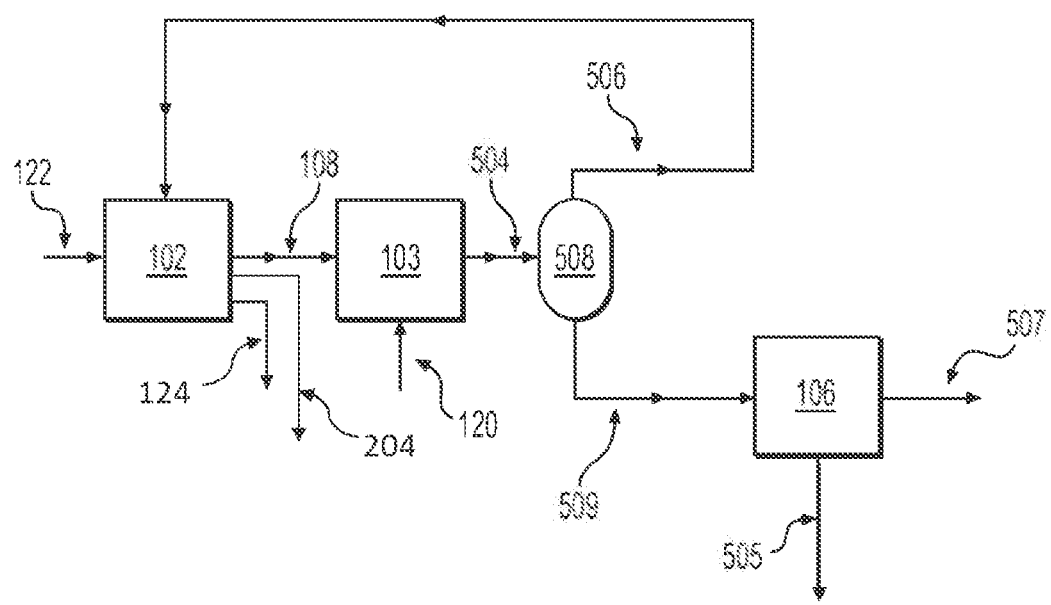
FIG. 5 is a schematic flow diagram illustrating the process steps of a non-integrated base steam cracking process and products produced therefrom.

Referring now to FIG. 5 where a non-integrated steam cracking process is illustrated. A second hydrocarbon feedstock passes through a line (122) into a steam cracking unit (102) to form a pyrolysis gasoline stream (108), a heavy pyrolysis oil stream (204), and a second light olefins stream (124). The pyrolysis gasoline stream (108) is fed to a hydro-processing unit (103), in the presence of hydrogen gas (120) to produce a hydro-processed pyrolysis gasoline stream (504). In some embodiments, there is an additional stream of pyrolysis oil exiting the hydro-processing unit (103) and entering the fuel oil pool. Flowing the hydro-processed pyrolysis gasoline stream (504) to a splitter (508) to form a $C_5/C_6$ stream (506) and an aromatic rich stream (509), the $C_5/C_6$ stream (506) is recycled to the steam cracking unit (102) to produce the second light olefins stream (124), while the aromatic rich stream (509) is passed to an extraction unit (106) to produce an aromatic rich stream (505), and a raffinate stream (507), which is optionally recycled to the steam cracker. The aromatic rich stream (505) may further be processed in a conventional manner.

Petrochemical refinement processes are known to be limited in their ability to simultaneously produce olefin and aromatic rich streams from multiple feedstock streams due to the need to hydro-process different feedstocks separately. Therefore, a process for producing an olefin and aromatic rich streams that incorporates combining and treating different feedstocks in a single hydro-processing procedure and/or process would be advantageous.

According to a first aspect, the present disclosure relates to an integrated process for forming a combined feedstock stream comprising a pyrolysis gasoline stream (108) and a full range cracked naphtha stream (109) to produce a plurality of olefin streams and a plurality of aromatic hydrocarbon streams. The process involves catalytically cracking a first hydrocarbon feedstock in a catalytic cracking unit (101) to form a full range cracked naphtha stream (109) and a first light olefins stream (125).

"Catalytically cracking" (catalytic cracking) as used herein refers to any process wherein a hydrocarbon feedstock is heated to a sufficient temperature in the presence of a cracking catalyst to undergo a cracking reaction, an isomerization reaction, a hydrogen transfer reaction, a coking reaction, and/or any combination thereof and form a naphtha stream and/or an olefins stream (e.g., a full range cracked naphtha stream (109)) comprising lower weight hydrocarbon components relative to the first hydrocarbon feedstock components and/or lower molecular weight olefinic materials. Catalytic cracking processes, cracking reactions, isomerization reactions, hydrogen transfer reaction and coking reaction are all well known in the art. In one embodiment the catalytic cracking is a fluid catalytic cracking. Typical catalytic cracking products include but are not limited to fuel gas, liquefied petroleum gas (LPG), gasoline, naphtha, light cycle oil (LCO), and heavy oil. Desirable chemical components of the catalytic cracking products such as light olefins (ethylene, propylene, and/or butadiene), and aromatics (such as benzene toluene, xylenes and ethyl benzene) may be recovered in varying quantities with additional processing.

The first hydrocarbon feedstock may be selected from any hydrocarbon mixture containing at least one of an aromatic component, a polyaromatic component, a mono-olefin component, a paraffin component, a naphthene component, an alkylnaphthene component, and/or any combination thereof. Exemplary first hydrocarbon feedstocks include but are not limited to mineral oil, crude oil, naphtha, light gasolines, gas oils, lubricating oil, fuel oil, residue and/or any combination thereof.

The first hydrocarbon feedstock may have a mono-olefin content by weight of at most 20%, at most 15%, at most 10%, at most 5%, or at most 1%, based on the total weight of the hydrocarbon feedstock, preferably 0%-9%, 0%-5%, 0%-3% or 0%-1% by weight. The first hydrocarbon feedstock may also have a density ranging from 0.800-0.950 g/cm$^3$, preferably 0.850-0.920 g/cm$^3$, more preferably 0.870-0.900 g/cm$^3$.

As used herein "by weight" refers to a numerical value calculated based on the total weight of the respective hydrocarbon stream/feedstock. A sufficient temperature as used herein refers to a temperature range of 300° C.-600° C., preferably at least 300° C., at least 325° C., at least 350° C., at least 400° C., at least 425° C., at least 450° C., at least 500° C., at least 525° C., or at least 550° C.

The catalytic cracking unit includes at least one riser which is optionally fluidly connected to at least one of each of the following, a separator, and a regenerator which is optionally fluidly connected to at least one fractionator. Typically, the riser is an elongated vessel with at least one hydrocarbon feedstock inlet, at least one gas inlet, a contact zone, and a bed of finely divided cracking catalyst maintained within the contact zone and serves as the site of the hydrocarbon/catalyst reaction.

The bed of finely divided cracking catalyst may be in a fluid state (Fluid Catalytic Cracking or FCC) or a static state. The fluid state may be maintained by continuously flowing a gas, such as a gaseous hydrocarbon mixture, or steam through the bed of catalyst. The separator includes a separating zone comprising at least one disengaging device such as a cyclone separator and a catalyst stripper. The main fractionator is a housing which includes a condensing zone and at least one distillation column while the regenerator includes at least one oxidizing zone comprising a heating source and an oxidizing gas. Features including the riser, separator, regenerator, catalyst stripper, cracking catalyst and fractionator are well known in the art.

An exemplary catalytic cracking process within a fluid catalytic cracking unit may include preheating a hydrocarbon feedstock to a temperature range of 205° C.-400° C., atomizing the preheated hydrocarbon feedstock via the hydrocarbon feedstock inlet into the contacting zone, contacting the preheated hydrocarbon feedstock with the bed of cracking catalyst in a catalyst/hydrocarbon feedstock ratio from 4:1-10:1 by weight, at a riser temperature range of 495° C.-735° C. for an appropriate residence time, to initiate the cracking reaction and form a cracked hydrocarbon/catalyst vapor mixture, passing at least a portion of the cracked hydrocarbon/catalyst mixture to the separating zone at an outlet vapor rate of 10-20 m/s where the cracked hydrocarbon/catalyst mixture is rapidly separated by at least one cyclonic separator to form an entrained catalyst stream and a first full range cracked naphtha vapor stream. Stripping the entrained catalyst stream in the catalyst stripper under a steam flow liberates entrained cracked naphtha vapors and forms a spent catalyst stream and a second cracked naphtha vapor stream. Regenerating the spent catalyst stream in the regenerator for use in the riser, and condensing the first full range cracked naphtha vapor stream, the second full range cracked naphtha vapor stream or both into a liquid phase in the condensing zone to form a full range cracked naphtha stream. Optionally, the full range cracked naphtha stream may be distilled in the distillation column to produce a plurality of hydrocarbon streams including but not limited to $C_3/C_4$ streams, gasoline, and fuel gas.

The cracking catalyst as used herein may comprise at least one metal attached to a support material. Exemplary metals may include one or more group 6, 8, 9, 10, 11 metals, preferably molybdenum, cobalt, nickel, tungsten, gold, gallium, aluminum, iron, platinum, iridium, palladium, osmium, silver, rhodium, and/or ruthenium.

The support material may be selected from materials such as a molecular sieves, alumina, and silica-alumina, tectosilicates, and zeolites. In the case of molecular sieves preferably, large-pore molecular sieves comprising a pore diameter of at least 0.7 nm, medium pore molecular sieves comprising a pore diameter between 0.5-0.7 nm, and/or both may be used. Preferably the support comprises a tetrahedral framework oxide component.

An appropriate residence time as used herein refers to a time period required to convert 75%-99%, preferably at least 90%, at least 91%, at least 92%, at least 93%, at least 94%, at least 95%, at least 96%, at least 97%, or at least 98%, by weight of the hydrocarbon feedstock contacting the cracking catalyst within the reactor riser contact zone into the cracked hydrocarbon/catalyst vapor mixture in the contact zone of the riser. The appropriate residence time may vary depending upon the chemical component composition of the hydrocarbon feedstock and may determine the amount of low molecular weight, high volatility hydrocarbon components produced from a first hydrocarbon feedstock. An exemplary appropriate residence time range may be about 1.0-5.0 seconds, preferably about 1.0-3.0 s.

The full range cracked naphtha stream (109) may include hydrocarbon components selected from but not limited to naphthenes; olefins such as phenyl acetylene, methyl-1-butadiene, 3-methyl-1-butadiene, 3,3-dimethyl-1 butadiene, 2,3-dimethyl-1-butadiene,hexene, 1-hexene, 1-pentene, 3,3-dimethyl-1-butadiene, 2,3-dimethyl-1-butadiene, 1-heptene, 1-octene, 2,3,3-trimethyl-1-pentene, 2-ethyl-1-hexene, 1-decene; 1-undecene, 1-dodecene, 1-tetradecene, 1-hexadecene, 1-octadecene, 1-eicosene, and alpha olefins; di-olefins such as methylpentadiene, phenyl butadiene isoprene, piperylene, 1,3-hexadiene, 3,4-dimethyl-1,3-hexadiene, 1,3-octadiene, 2,4-decadiene and cyclopentadiene; polyolefins; paraffins; aromatics/polyaromatics such as benzene ($C_6$), toluene ($C_7$), xylenes ($C_8$), naphthalene, mono-alkylnaphthalenes such as 1-methyl-naphthalene and 3-ethylnaphthalenes, di-alkylnaphthalenes such as 1,2-dimethylnaphthalene, 1,2-diethylnaphthalene 2,3-dimethylnaphthalene, 2,3-dipropylnaphthalene 2,6-dimethylnaphthalene, 2,6-dibutyl-naphthalene, phenanthrene, anthracene, indane, pyrene, and biphenyl; $C_9$ Aromatics ($C_9$) such as ethyl benzene, $C_{10+}$ aromatics; ($C_{10+}$) such as 1,4-diethylbenzene, 1,2-diethylbenzene, 1,3-diethylbenzene, triethylbenzenes 1,3,5-triethylbenzene, propylbenzenes, dipropylbenzenes, tripropylbenzenes, isopropylbenzenes, diisopropylbenzenes, triisopropylbenzenes, methylethylbenzenes, dimethylethylbenzenes, trimethylethylbenzenes, methyldiethylbenzenes, dimethyldiethylbenzenes, trimethyldiethylbenzenes, methyltriethylbenzenes, dimethyltriethylbenzene, methylpropylbenzenes, dimethylpropylbenzenes, trimethylpropylbenzenes, ethylpropylbenzenes, diethylpropylbenzenes, triethylpropylbenzenes, mesitylene (1,3,5-trimethylbenzene), hemimellitene (1,2,3-trimethylbenzene), pseudocumene (1,2,4-trimethylbenzene), tetramethylbenzene, and 1,2,4,5-tetramethylbenzene; Non-aromatic cyclic hydrocarbons such as alkylcyclopentanes methylcyclopentane, ethylcyclopentane, alkylcyclopentenes, methylcyclopentene, ethylcyclopentene, cyclohexane, alkylcyclohexanes, methylcyclohexane, ethylcyclohexane, cyclohexenes, methylcyclohexene, ethylcyclohexene, dihydrocyclopentadienedimer, tetrahydrocyclopentadienedimer, decalins, cyclopentadienes, cyclohexadienes, ethylmethylcyclopentane and dimethylcyclopentane; non-cyclic alkanes such as iso-pentane, pentane, iso-hexane, and hexane; nitrogen compounds such as pyridine, pyrrole, and porphyrins; sulfur compounds such as sulfur, hydrogen sulfide, methyl mercaptan, phenyl mercaptan, cyclohexylthiol, dimethyl sulfide, hydrogen sulfide, and thiocyclohexane and/or any combination thereof.

Aromatic/polyaromatic as used herein refers to any cyclic hydrocarbons comprising at least one aromatic ring within the compounds molecular structure. However when the terms are used separately polyaromatic refers explicitly to cyclic hydrocarbons comprised of at least two aromatic rings while aromatic maintains the earlier definition.

Aromatically rich (aromatic-rich and/or rich in aromatics) as used herein refers to any hydrocarbon stream and/or feedstock with an aromatic content, polyaromatic content or both by weight that is at least 10%, at least 20%, at least 30%, at least 40%, at least 50%, at least 60%, at least 70%, at least 80% or at least 90%, preferably 20%-90%, more preferably 20%-50% of the total hydrocarbon stream.

Olefins as used herein refers to a class of hydrocarbon components containing at least one carbon-carbon double bond in their structure and include mono-olefins, di-olefins and/or any combination thereof unless otherwise defined.

The full range cracked naphtha stream (109) may comprise by weight, 5%-50%, preferably 10%-45%, 15%-40%, 20%-35%, or 25%-30% mono-olefins; 5%-50%, preferably preferably 10%-45%, 15%-40%, 20%-35%, or 25%-30% paraffins; 5%-60%, preferably 10%-55%, 15%-50%, 20%-45%, 25%-40%, or 30%-35% aromatics/polyaromatics; 5%-40%, preferably 10%-35%, 15%-30%, or 20%-25% naphthenes; 50-400 ppmw, preferably 150 ppmw-350 ppmw, 250 ppmw-300 ppmw sulfur and/or any combination thereof.

The first light olefins stream (125) as used herein refers to an olefin-rich output stream from the catalytic cracking unit (101) comprising mainly lower molecular weight olefin components preferably one or more of butadiene, ethylene, propylene and/or any combination thereof. The first light olefins stream (125) may be 10-70% by weight, preferably 15-65%, 20-60%, 20-55% of the total low molecular weight olefin component output from the catalytic cracking unit (101) using the first hydrocarbon feedstock. The lower molecular weight olefin components represent at least 20% by weight, preferably at least 30%, at least 40%, at least 50%, at least 60%, at least 70% at least 80% at least 90% at least 95% by weight of the first light olefins stream (125).

The first light olefins stream (125) contains compounds having a relatively lower molecular weight and higher volatility than the full range cracked naphtha stream (109) and is typically separated from the full range cracked naphtha stream (109) by distillation through one or more distillation columns within or outside the catalytic cracking unit (101). The first light olefins stream (125) may be obtained by distillation outside of the catalytic cracking unit (101). The first light olefins stream (125) may be obtained as the lights and/or overhead from the distillation. Likewise, the full range cracked naphtha stream (109) may represent a bottoms product and/or an intermediate product having a volatility less than the average volatility of the first olefins stream (125) but higher than the average volatility of a bottoms product that remains after the first light olefins stream (125) is removed from a typical non-integrated catalytic cracking unit (101) output (see for example FIG. 4).

Alternatively a portion of the first light olefin stream (125) may be combined or included with the full range cracked naphtha stream (109) to increase the olefin content of the combined stream (110).

The process of the present disclosure also includes steam cracking (102) a second hydrocarbon feedstock in a steam cracking unit to form a heavy pyrolysis oil stream (204), pyrolysis gasoline stream (108) and a second light olefins stream (124).

"Steam cracking" (STC) as used herein refers to any process that includes heating a hydrocarbon feedstock in the presence of steam to an appreciable temperature to initiate a pyrolysis reaction in order to break carbon-carbon bonds; quenching the pyrolyzed hydrocarbon product to form a quenched hydrocarbon product and fractioning the quenched hydrocarbon product to form a heavy pyrolysis oil stream (204), pyrolysis gasoline stream (108) and a second light olefins stream (124).

The pyrolysis gasoline stream (108) may include components selected from but not limited to olefins, diolefins, polyolefins, paraffins, aromatics/polyaromatics, alkanes, non-aromatic cyclic hydrocarbons and/or any combination thereof. Steam cracking processes as well as the pyrolysis reaction, temperature conditions, quenching, and fractioning steps are well known in the art.

In one embodiment, the light pyrolysis oil stream (130) comprises an asphaltene phase and/or a deasphalted phase, wherein the asphaltene phase has a substantial amount of low/medium range molecular weight polyaromatic structures such as asphaltene and other hydrocarbon resins in the preferable range of $C_{15}$-$C_{50}$. In one embodiment, the light pyrolysis oil stream (130) further comprises dicyclopentadiene.

In one embodiment, the heavy pyrolysis oil stream (204) contains an asphaltene phase and/or a deasphalted phase, wherein the asphaltene phase has a substantial amount of high molecular weight polyaromatic structures such as asphaltene and other complex hydrocarbon resins in the range of $C_5$-$C_{100+}$, and more preferably $C_{50}$-$C_{80}$. In one or more embodiments, the heavy pyrolysis oil stream (204), may be used for production of asphalt, syngas, and/or fuel oil. In one embodiment, the heavy pyrolysis oil stream (204), may be used as a feed to a coking unit to convert a portion of the high molecular weight polyaromatic structures into low molecular weight hydrocarbon compounds, and to use the low molecular weight hydrocarbon compounds as a feedstock for the steam cracking unit.

The second light olefins stream (124) as used herein refers to an olefin-rich output stream from the steam cracking unit (108) comprising mainly lower molecular weight olefin components relative to the second hydrocarbon feedstock components, preferably one or more of butadiene, ethylene, propylene and/or any combination thereof. The second light olefin stream (124) represents 5-50% by weight, preferably 10%-45%, 15%-40%, 20%-35% by weight of the total low molecular weight olefin component output from the steam cracking unit using the second hydrocarbon feedstock.

Lower molecular weight components such as ethylene and propylene may represent at least 20% by weight, preferably at least 30%, at least 40%, at least 50%, at least 60%, at least 70% at least 80% at least 90% at least 95%, preferably 20-90%, 30-60% or 40-80% by weight of the total second light olefins stream (124).

The second light olefins stream (124) contains compounds having relatively lower molecular weight and higher volatility than the full range cracked naphtha stream (109) and is typically separated from the pyrolysis gasoline stream (108) by distillation through one or more distillation columns within the steam cracking unit (102). Alternatively the second light olefins stream (124) may be obtained by distillation outside of the steam cracking unit (102). The second light olefins stream (124) may be obtained as the lights and/or overhead from a distillation. Likewise, the pyrolysis gasoline stream (108) may represent a bottoms product and/or an intermediate product having a volatility less than the volatility of the average volatility of the second light olefins stream (124) but higher than the average volatility of a bottoms product that remains after the second light olefins stream (124) is removed from a typical steam cracking unit's output.

Alternatively, the second light olefin stream (124) may be combined with included with the pyrolysis gasoline stream (108) to increase the olefinic content of the combined stream (110).

Hydrocarbon feedstocks used in the steam cracker may include a variety of chemical classes which are well known in the art. Exemplary classes include refinery gases ($C_1$-$C_4$), liquefied petroleum gas ($C_3$-$C_4$), naphtha ($C_5$-$C_{17}$), gasoline ($C_4$-$C_{12}$), kerosene/diesel fuel ($C_8$-$C_{18}$), aviation fuel ($C_8$-$C_{16}$), fuel oil ($C_{20+}$), lubricating oil ($C_{20+}$), wax ($C_{17+}$), asphalt ($C_{20+}$), coke ($C_{50+}$), crude oil and/or any combination thereof. Each respective class may be described by a boiling/volatility range.

In one embodiment a Saudi Arabian crude oil comprises fractions with a boiling range under 1 atmosphere of pressure of less than 0° C. refinery gases (dry/wet), 32° C.-182° C. naphtha, 193° C.-271° C. kerosene, 271° C.-321° C. light gas oil, 321° C.-427° C. heavy gas oil, 371-566° C. vacuum gas oil, and more than 566° C. residue.

Each feedstock class possesses a boiling point range and a carbon atom distribution that may vary between feedstocks largely due to regionally defined differences in composition and extraction methods, and as a result may produce different petrochemical products when undergoing refining processes.

In one embodiment, a Saudi Arabian light crude oil comprises about 2% refinery gases ($C_1$-$C_2$), 20%-26% naphtha ($C_{20}$-$C_{26}$), 7%-12% kerosene ($C_7$-$C_{12}$), 10%-14% wax ($C_{17}$-$C_{22}$), and 35%-40% residue ($C_{20}$-$C_{90}$).

The chemical components which were previously described hereinabove for the first hydrocarbon feedstock may be present in the second hydrocarbon feedstock as well.

The second hydrocarbon feedstock as used herein may be selected from but not limited to mineral oil, crude oil, naphtha, light gasolines, gas oils, lubricating oil, fuel oil, residue and/or any combination thereof and includes a diolefin hydrocarbon content by weight of at most 20%, at most 15%, at most 10%, at most 5%, or at most 1%, based on the total weight of the hydrocarbon feedstock, preferably 0%-10%, 0%-5%, 0%-3% or 0%-1% by weight. The second hydrocarbon feedstock may also have a density ranging from 0.800-0.950 g/cm$^3$, preferably 0.850-0.920 g/cm$^3$, more preferably 0.870-0.900 g/cm$^3$.

The steam cracking unit (102) itself may include at least one pyrolysis furnace optionally fluidly connected to at least one heat exchanger which is optionally fluidly connected to at least one adjacent primary fractionating column. The at least one pyrolysis furnace may comprise one or more of a convection stage, a radiation stage optionally traversed by a plurality of fluidly connected tubes for carrying the second hydrocarbon feedstock from a convection stage inlet through a convection stage interior to a radiation stage interior and terminating at a radiation stage outlet. The pyrolysis furnace may be operated at low pressure range of 100-300 kPa, preferably 120-280 kPa, more preferably 160-240 kPa, to account for a higher molar output of pyrolyzed hydrocarbon product compared to a molar input of the second hydrocarbon feedstock.

An exemplary steam cracking process within a steam cracking unit may include: a second hydrocarbon feedstock passing through the plurality of fluidly connected tubes is preheated and mixed with steam in a convection stage interior to a temperature of at least 400° C., at least 425° C., at least 450° C., at least 475° C., at least 500° C., at least 525° C., at least 550° C., or at least 575° C., or at least 600° C., preferably 400-600° C. or about 500° C., before being passed to a radiation stage. Within the radiation stage at least one array of burners rapidly heats at least a portion of the second hydrocarbon feedstock to a sufficient temperature to form the pyrolyzed hydrocarbon product.

Steam cracking residence time as used herein refers to the time period required to convert the hydrocarbon feedstock to a pyrolyzed hydrocarbon feedstock in a radiant stage. The steam cracking residence time may vary depending upon the chemical components of the hydrocarbon feedstock as well and may determine the amount of low molecular weight, high volatility hydrocarbon components produced from a hydrocarbon feedstock. An exemplary STC residence time range may be about 0.08-0.8 seconds, preferably about 0.1-0.5 s.

The steam cracking continues with the pyrolyzed hydrocarbon product being passed through the radiation stage outlet to a fluidly connected heat exchanger where rapid quenching lowers the pyrolyzed hydrocarbon feedstock temperature to stabilize the pyrolyzed hydrocarbon product composition and terminate the pyrolysis reaction. An exemplary quenching occurs within less than 0.01 s, 0.02 s, 0.03 s, 0.04 s, 0.05 s, 0.5 s, 1.0 s, or 10 s of the pyrolyzed hydrocarbon feedstock exiting the radiant stage. Heat exchangers are well known to those skilled in the art with an exemplary heat exchanger being a quenching boiler.

Finally, at least one adjacent fractionating column which are well known by those skilled in the art, may then divide the quenched hydrocarbon feedstock to form the pyrolysis gasoline stream.

The mass ratio of steam to the second hydrocarbon feedstock in the convection stage mixing may be used to increase the output of light olefins depending upon the hydrocarbon feedstock used. The mass ratio of steam to hydrocarbon by weight for a second hydrocarbon feedstock may be at least 30%, at least 35%, at least 40%, at least 45%, at least 50%, at least 55%, at least 60%, at least 65%, at least 70%, at least 75%, or at least 80%, preferably 30-80%, 40-70% or 50-60% by weight.

The pyrolysis gasoline stream (108) may include by weight 5-50%, preferably 5%-25%, 30%-50% mono-olefins; 5-50%, preferably 5-25%, 30-50% paraffin; 10-70% 10%-45%, 50%-70% diolefins; 25-70%, preferably at least 25%-45%, 50%-70% aromatics/polyaromatics, 1-20 ppmw, preferably 2 ppmw-15 ppmw, 3 ppmw-10 ppmw sulfur and/or any combination thereof.

The present disclosure also relates to combining and/or mixing (123) at least a portion of each of the full range cracked naphtha stream (109) and the pyrolysis gasoline stream (108) to form a combined stream (110).

The combining and/or mixing (123) as used herein may refer to any continuous and/or batch process wherein at least two hydrocarbon streams are combined into a single stream. In order to establish, maintain, and/or alter component content within the combined stream (110), the mixing (123) may be used to alter the ratio of the full range cracked naphtha (109), to the pyrolysis gasoline (108) or vice versa within the combined stream (110). As a result, the mixing (123) is a particularly useful process step for providing specific feed streams directed towards different petrochemical product lines.

The combined stream (110) as used herein refers to a hydrocarbon stream resulting from at least two separate and distinct hydrocarbon feeds in any chemical, and/or physical state of matter (e.g. solid, liquid, gas) undergoing a mixing process to produce a single hydrocarbon stream.

The combined stream (110) may comprise by weight, 5%-30%, preferably 10%-25%, or 15%-20%, mono-olefins; 5%-30%, preferably 10%-25%, or 15%-20% paraffin; 5%-60%, preferably 10%-55%, 15%-50%, 20%-45%, 25%-40%, or 30%-35%, aromatics/polyaromatics; 1%-20%, preferably 3%-15%, or 4%-10% naphthenes; 1%-30% preferably 3%-25%, or 5%-20% di-olefins; 10-200 ppmw, preferably 20 ppmw-150 ppmw, 30 ppmw-100 ppmw sulfur and/or any combination thereof.

In one embodiment, the combined stream (110) comprises by weight 5%-99%, preferably, 15%-95%, 20%-90%, 25%-85%, 30%-80%, 35%-75%, 40%-70%, 45%-65%, or 50%-60%, full range cracked naphtha stream (109); 5%-99%, preferably, 15%-95%, 20%-90%, 25%-85%, 30%-80%, 35%-75%, 40%-70%, 45%-65%, or 50%-60%, pyrolysis gasoline stream (108).

In one embodiment, the mixing (123) produces a combined stream (110) comprising at least 16% diolefins by weight, from a full range cracked naphtha stream (109) comprising less than 1% diolefins and a pyrolysis gasoline stream comprising at least 22% by weight.

The respective component contribution of the full range cracked naphtha stream (109), and/or the pyrolysis gasoline stream (108) to the total component(s) composition of the combined stream (110) may include a weight percent distribution of 50%-99%, preferably at least 50%, at least 55%, at least 60%, at least 65%, at least 70%, at least 75%, at least 80%, at least 85%, at least 90%, at least 95%, at least 99%, by weight of the total component(s) composition within the combined stream (110).

Alternatively, the volumetric ratio of the full range cracked naphtha stream (109) to the pyrolysis gasoline stream (108) in the combined stream (110) or vice versa may include a range of 1:10 to 10:1, preferably 1:9 to 9:1, 1:8 to 8:1, 1:7 to 7:1, 1:6 to 6:1, 1:5 to 5:1, 1:4 to 4:1, 1:3 to 3:1, 1:2 to 2:1 or 1:1.

The mixing/combining (123) may require the steam cracking unit (102) and the catalytic cracking unit (101) to be connected or optionally fluidly connected by pipes and include at least one intersection point. Preferably, the at least one intersection point is the site of the mixing (123). The at least one intersection point may include a plurality of single, and/or multidirectional flow controllers such as valves for controlling the flow rate of the pyrolysis gasoline stream (108), the full range cracked naphtha stream (109) or both into the at least one intersection point.

Additionally, the mixing (123) may occur at a sufficient distance from the steam cracking unit (102), the catalytic cracking unit (101) or both to decrease heat lost in the full range cracked naphtha stream (109), the pyrolysis gasoline (108) or both and increase the efficiency of the hydro-processing.

"Sufficient distance" as used herein refers to any distance where a difference in the initial temperature and final temperature of a traversing hydrocarbon stream is equal to or less than 20° C., equal to or less than 15° C., equal to or less than 10° C., equal to or less than 5° C. In one embodiment the pyrolysis gasoline (108), the full range cracked naphtha stream (109) or both undergo the mixing (123) with a less than 3° C. temperature loss.

Reducing heat lost in the full range cracked naphtha stream (109), the pyrolysis gasoline stream (108) and subsequently the combined stream (110) may provide a significant advantage during the hydro-processing. Prior to hydro-processing, feed streams such as the full range cracked naphtha stream (109) and/or the pyrolysis gasoline stream (108) are typically subjected to a preheating stage in order to reduce the energy required to at least partially hydrogenate the feed stream's components. The preheating energy source may be at least one dedicated heating unit, a heated gas stream from other stages of the hydro-processing unit, a refinery process, and/or both. Providing a combined stream having a temperature at or near a preheating temperature decreases the energy requirement for operating the hydro-processing unit by allowing the combined stream to pass directly into the more reactive stages of the hydro-processing, and freeing the preheating energy source for use in other refinery processes.

In order to provide a hydrocarbon stream of a consistent composition to the hydro-processing unit (103) during power outages, equipment failure, turnarounds, maintenance services, or anything that causes the units located upstream of the hydro-processing unit (103) to go out of operation, the full range cracked naphtha stream (109), the pyrolysis gasoline (108) or both may each have at least one designated storage vessel. The respective storage vessels may be connected downstream of the respective cracking units, but upstream of the mixing intersection point (123), the hydro-processing unit (103) or both. In one embodiment, at least one storage vessel is fluidly connected to the catalytic cracking unit (101), and the steam cracking unit (102) prior to the intersection point (123).

The process also includes hydro-processing the combined stream (110) in a hydro-processing unit (103) to form a hydro-processed combined stream (111), and a light pyrolysis oil stream (130).

Hydro-processing as used herein may refer to any process where a hydrocarbon stream is reacted in a hydro-processing unit (103) with hydrogen gas in the presence of at least one catalyst to at least partially hydrogenate mono-olefins, diolefins and/or aromatic/polyaromatic components, and/or remove or reduce the amount of sulfur, nitrogen, oxygen, and metals (e.g. arsenic, lead, etc.) from the hydrocarbon stream. Exemplary nitrogen and sulfur containing components include pyridine, pyrrole, porphyrins, hydrogen sulfide, methyl mercaptan, phenyl mercaptan, cyclohexylthiol, dimethyl sulfide, hydrogen sulfide, and thiocyclohexane.

A hydro-processing unit (103) typically comprises a preheating zone, optionally fluidly connected to at least one hydro-processing reactor, optionally fluidly connected to a separating zone optionally connected to a fractionation zone. The at least one hydro-processing reactor may include at least two stages composing at least one layer/bed of a hydro-processing catalyst, with at least one quenching zone optionally separating the stages.

An exemplary hydro-processing unit (103) operation may optionally include preheating the combined gas stream (110) in a preheating zone to a temperature of at least 250° C., and mixing the preheated combined stream with a preheated hydrogen gas flow to form a hydrogen/combined gas mixture within a pressure range of for example 490 psig-1600 psig, contacting the hydrogen/combined gas mixture with a first hydro-processing catalyst in a hydro-processing reactor's first stage to at least partially hydrogenate diolefins and form mono-olefins at a temperature range of 60-150° C. and a reaction pressure range of for example 490 psig-1600 psig, contacting the hydrogen/combined gas stream with a cold hydrogen gas stream in the quenching zone to lower the hydrogen/combined gas mixture temperature, separating the $C_{10+}$ material as light pyrolysis oil stream (130), reacting the quenched hydrogen/combined gas mixture with a second hydro-processing catalyst in a second stage to at least partially hydrogenate mono-olefins into naphthenes and convert components containing sulfur, nitrogen, metals (e.g. arsenic, lead, etc.), and/or any combination thereof into sulfides, ammonia, and metal sulfides respectively at a temperature range of 275° C.-450° C. and a reaction pressure range of 490 psig-1600 psig, removing the sulfides, ammonia, metal sulfides, excess hydrogen, and/or any combination thereof in the separating zone to produce a hydro-processed combined mixture at a temperature range of 60° C.-400° C. and a reaction pressure range of 450 psig-1550 psig, and dividing the hydro-processed combined gas mixture in the fractionating zone to produce a hydro-processed combined stream wherein the operating conditions of the fractionating zone include a temperature range from 40° C.-450° C. and a pressure range of about 0.7 psig-290 psig.

In one embodiment, the hydro-processing is a two stage process comprising a) hydrogenating the combined stream (110) with a first hydro-processing catalyst to convert one or more diolefins present in the combined stream (110) into one or more mono-olefins in a first stage to produce a quenched hydrogen/combined gas mixture, and b) saturating the quenched hydrogen/combined gas mixture with a second hydro-processing catalyst to convert mono-olefins into paraffins, partially convert aromatics to naphthenes, and components containing sulfur, nitrogen, metals (e.g. arsenic, lead, etc.), and/or any combination thereof into sulfides, ammonia, and metal sulfides in a second stage wherein the second hydro-processing catalyst may be for example a Ni/Mo or a Co/Mo catalyst.

The first hydro-processing catalyst, the second hydro-processing catalyst, or both may include at least one metal attached to a support material. Exemplary metals may include group 6, 8, 9, 10, 11 metals, molybdenum, cobalt, nickel, tungsten, gold, platinum, iridium, palladium, osmium, silver, rhodium, and/or ruthenium. The support material may be selected from materials such as a molecular sieves, alumina, and/or silica-alumina.

As a note, the first hydro-processing catalyst and second hydro-processing catalyst may be different catalysts or similar depending upon the combined stream feedstock composition, and hydro-processing conditions.

In embodiments of the invention, the combined hydrocarbon stream is subject to hydro-processing in the hydro-processing unit, whereby the major portions of di-olefin components and mono-olefin components are saturated to form saturated products including naphthenes, paraffins, and/or aromatics/polyaromatics. In one embodiment, preferably 50-99.5% by weight of the total amount of diolefin, mono-olefins and, optionally aromatic components that are subject to the hydro-processing are fully or partially saturated such that most carbon-carbon double bonds are reduced, more preferably 60-99%, 70-98%, 80-95%, or about 90% by weight of the of the total amount of diolefin, mono-olefins and, optionally aromatic components are hydrogenated. In one embodiment, up to and including 99% of the diolefins by weight are saturated during the hydro-processing.

In one embodiment, at least 98% of the mono-olefins by weight are saturated during the hydro-processing to form paraffins and aromatics to naphthenes.

Alternatively, aromatic component saturation during the hydro-processing may be minimized in order to increase the aromatic content of the hydro-processed combined stream (111).

Minimizing as used herein refers to any process wherein at least one reaction parameter for a hydro-processing unit is altered in order to provide a hydrocarbon output stream (e.g., the hydro-processed combined stream (111)) with a weight percentage of saturation relative to a hydrocarbon input stream (e.g. the combined hydrocarbon stream (110)) that is within a preferred range. Exemplary parameters include but are not limited to reaction temperature, stream flow rate, reaction time, hydrogen gas pressure and or any combination thereof.

The hydro-processing may saturate by weight 1-10%, preferably less than 9%, preferably less than 8%, preferably less than 7%, preferably less than 6%, preferably less than 5%, preferably less than 4%, preferably less than 3%, preferably less than 2%, of the total aromatic content of the combined hydrocarbon stream (110).

Minimizing aromatic saturation may also decrease the amount of heat energy released during the hydroprocessing, resulting in fewer technical challenges. Exemplary technical challenges may include but are not limited to catalyst deactivation, product stream degradation, hydro-processing unit structural failure, and/or any combination thereof. In one embodiment, the amount of heat energy released during the hydro-processing when aromatic saturating is minimized is 10-60%, preferably 15-50%, preferably 20-40%, preferably 30-35% relative to the total amount of heat released when aromatic saturating is not minimized.

The hydro-processing stages may be operated independently or in conjunction with each other depending upon the mono-olefin content, diolefin content, aromatic/polyaromatic content, sulfur content, nitrogen content, metals content, and/or any combination thereof desired within the hydro-processed combined stream (111). In one embodiment, the hydro-processing forms a hydro-processed combined stream (111) having a sulfur content of less than 2 ppm.

The use of independently operated stages in the hydro-processing may allow the disclosed process to continuously or periodically yield a hydro-processed combined stream (111) with comparable component content to hydro-processed hydrocarbon streams using separate hydro-processing steps, while maintaining the ability to provide hydro-processed combined stream (111) batches to meet evolving petrochemical product demands for olefins, aromatics/polyaromatics, fuel oils, and/or any combination thereof.

In addition to the hydro-processed combined stream (111), the light pyrolysis oil stream (130) is also received from the output of the hydro-processing unit (103). In one embodiment, the light pyrolysis oil stream (130) contains an asphaltene phase and/or a deasphalted phase, wherein the asphaltene phase has a substantial amount of low/medium range molecular weight polyaromatic structures such as asphaltene and other hydrocarbon resins in the preferable range of $C_{15}$-$C_{50}$. In one embodiment, the light pyrolysis oil stream (130) also comprises dicyclopentadiene.

In cases, where the full range cracked naphtha stream may have a low di-olefin content, it may be possible to separately hydrogenate the pyrolysis gasoline stream in the first stage of the hydro-processing reactor and subsequently saturate both hydrocarbon streams (i.e. the full range cracked naphtha stream and the "hydrogenated" pyrolysis gasoline stream) in the second stage. This may be a cost effective way of treating two or more hydrocarbon streams with different olefinic material compositions in a single hydro-processing unit, while still producing a hydro-processed combined stream rich in paraffins. In one embodiment, the full range cracked naphtha stream (109) is not hydrogenated in the first stage of the hydro-processing unit (103). In one embodiment the full range cracked naphtha stream (109) is passed overhead to the hydroprocessing reactor second stage wherein the full range cracked naphtha stream (109), bypasses the mixing and the first stage of the hydro-processing reactor.

A "low di-olefin content" as used herein, refers to a di-olefin content of less than 5%, preferably less than 4%, preferably less than 3%, preferably less than 2%, preferably less than 1%, preferably less than 0.5%, by weight of the total full range cracked naphtha stream.

The present disclosure also relates to splitting (104) the hydro-processed combined stream (111) into a $C_5$/$C_6$ stream (112), and a first aromatic rich stream (114) comprising $C_6$ molecules, $C_7$ molecules, $C_8$ molecules, $C_{9+}$ molecules or any combination thereof in a first splitter (104).

Splitting as used herein may refer to any process where a hydrocarbon mixture is separated by volatility, solubility and/or composition into at least two streams composing a range of hydrocarbons components. An exemplary splitting process is a distillation comprising at least one or more distillation columns and is well known by those skilled in the art.

The $C_5$/$C_6$ stream (112) as used herein refers to a hydrocarbon stream wherein the hydrocarbon components include mainly 5-6 carbon atoms in the form of straight chain paraffins, branched chain paraffins and/or any combination thereof. The $C_5$/$C_6$ stream may include a paraffinic content by weight of 10%-90%, preferably at least 10%, at least 15% at least 20%, at least 25%, at least 30%, at least 35%, at least 40%, at least 45%, at least 50%, at least 55%, at least 60%, at least 70%, at least 80%, or at least 85%. In one embodiment, the $C_5$/$C_6$ stream (112) comprises a paraffinic content by weight of at least 15%. In one embodiment, the $C_5$/$C_6$ stream (112) comprises only non-aromatic compounds having 5-6 carbon atoms.

The first aromatic rich stream (114) as used herein refers to an intermediate and/or bottom hydrocarbon stream from the first splitter (104) comprising aromatics/polyaromatics including benzene, toluene, xylenes, (BTX), $C_9$, $C_{10+}$, $C_{6+}$ non-aromatic cyclic hydrocarbons, $C_{6+}$ paraffinic hydrocarbon and/or any combination thereof.

The aromatic/polyaromatic content of the first aromatic rich stream (114) by weight is 10-90% preferably at least 10%, at least 15% at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%. In one embodiment, the first aromatic rich stream (114) comprises by weight an aromatic/polyaromatic content of at least 30%.

The present disclosure also relates to a second aromatic rich stream (119) and a heavy oil stream (115) that is formed by splitting the first aromatic rich stream (114) in a second splitter (107).

Similar to the first splitter (104), the second splitter (107) separates the first aromatic rich stream by hydrocarbon component volatility, solubility and/or composition. However, the volatility of the second aromatic rich stream (119) and the heavy oil stream (115) will be lower than the $C_5$/$C_6$ stream (112) and will require a higher average operating temperature for the second splitter (107) when compared to the first splitter (104).

The second aromatic rich stream (119) as used herein refers to a light overhead hydrocarbon stream from the second splitter (107) comprising aromatics such as benzene, toluene, xylenes, (BTX), $C_9$, $C_{6+}$ non-aromatic cyclic hydrocarbons, $C_{6+}$ paraffinic hydrocarbon and/or any combination thereof.

The second aromatic rich stream (119) may include an aromatic/polyaromatic hydrocarbon content of 30%-90% by weight, preferably at least 30%, at least 35%, at least 40%, at least 41%, at least 42%, at least 43%, at least 44%, at least 45%, at least 46%, at least 47%, at least 48%, at least 49%, at least 50%, at least 60%, at least 70%, at least 80%, or at least 90% by weight. In one embodiment, the heavy oil stream (115) comprises by weight at least 40% aromatic compounds, polyaromatic compounds and/or any combination thereof.

The heavy oil stream (115) as used herein refers to a column bottom oil fraction produced from the second splitter (107) and mainly includes aromatic/polyaromatic chemical components with at least $C_{9+}$, at least $C_{10+}$, at least $C_{11+}$, at least $C_{12+}$, at least $C_{13+}$, at least $C_{14+}$, at least $C_{15+}$, at least $C_{16+}$, at least $C_{17+}$, at least $C_{18+}$, at least $C_{19+}$, and/or at least $C_{20+}$ carbon atoms within the components molecular structure. In one embodiment, the heavy oil stream (115) comprises $C_{9+}$, aromatic/polyaromatic hydrocarbons, napthenes and paraffins. In one embodiment, the heavy oil stream (115) is sent to a fuel oil pool. In one embodiment, the heavy oil stream (115) comprises 10%-40% naphthalene ($C_{10}$), 1%-10% dimethyl benzene ($C_9$), 1%-10% biphenyl ($C_{12}$), and 1%-10% ethyl benzene ($C_9$) by weight.

The heavy oil stream (115) may include an aromatic and/or polyaromatic hydrocarbon content of 40-90% by weight, preferably at least 40%, at least 41%, at least 42%, at least 43%, at least 44%, at least 45%, at least 46%, at least 47%, at least 48%, at least 49%, at least 50%, at least 60%, at least 70%, at least 80%, or at least 90% by weight. In one embodiment, the heavy oil stream (115) comprises by weight at least 40% aromatic compounds, polyaromatic compounds and/or any combination thereof.

$C_{9+}$ aromatic hydrocarbons which may constitute 1-95%, preferably 10%-85%, 20%-75%, 30%-65%, 40%-55% of the heavy oil stream (115) could include ethylbenzene, methylethylbenzenes, 1,4-diethylbenzene, 1,2-diethylbenzene, and 1,3-diethylbenzene, methyldiethylbenzenes, dimethyldiethylbenzenes, trimethyldiethylbenzenes, dimethylethylbenzenes, trimethylethylbenzenes; triethylbenzenes such as 1,3,5-triethylbenzene, methyltriethylbenzenes; propylbenzenes such as dipropylbenzenes, tripropylbenzenes, isopropylbenzenes, diisopropylbenzenes, methylpropylbenzenes, dimethylpropylbenzenes, trimethylpropylbenzenes, ethylpropylbenzenes, diethylpropylbenzenes, triethylpropylbenzenes, dimethyltriethylbenzene; triisopropylbenzenestrimethylbenzenes such as mesitylene (1,3,5-trimethylbenzene), hemimellitene (1,2,3-trimethylbenzene), pseudocumene (1,2,4-trimethylbenzene) and tetramethylbenzene including durene (1,2,4,5-tetramethylbenzene).and/or any combination thereof.

In one embodiment, the process further comprises isomerizing the $C_5/C_6$ stream (112) in an isomerization unit (105) to form an isomerized stream (113).

Isomerizing as used herein refers to any process wherein a hydrocarbon stream comprising mainly straight chain paraffins are converted into branched chain iso-paraffins. Isomerization processes are well known by those of ordinary skilled in the art.

A typical isomerization unit comprises at least one isomerization reactor including at least one reaction zone, wherein the reaction zone comprises at least one layer/bed of a isomerization catalyst, at least one hydrocarbon feed inlet, at least one hydrogen gas inlet, and at least one product outlet. The at least one reactor is fluidly connected to a cooler, which is optionally, fluidly connected to a separator, which is connected to a stabilizer. Isomerization units including isomerization reactors, isomerization catalysts, coolers, separators and stabilizers are all well known by those skilled in the art. An exemplary isomerizing operation may include passing the $C_5/C_6$ stream (112) to the reaction zone of the isomerization reactor in the presence of hydrogen gas and a layer/bed of isomerization catalyst at a reaction temperature range of 120-180° C., preferably 130-160° C., and a reactor pressure of 300-500 psig, preferably 380-450 psig to undergo an isomerization reaction. Flowing the isomerized $C_5/C_6$ stream to a cooler wherein the cooler temperature range is 30-50° C., preferably 35-45° C., passing the cooled $C_5/C_6$ stream to the separator where the stream is separated into a vapor/gas phase stream, and a liquid phase isomerized stream (113).

The molar ratio of hydrogen gas to $C_5/C_6$ stream (112) in the isomerization reactor may range from 0.3 to 5.0, preferably at least 0.2, at least 0.4, at least 0.6, at least 0.8, at least 1.0, at least 1.2, at least 1.4, at least 1.6, at least 1.8, at least 2.0, at least 2.2, at least 2.4, at least 2.6, at least 2.8, at least 3.0, at least 3.2, at least 3.4, at least 3.6, at least 3.8, or at least 4.0.

The process of the present disclosure may further comprise extracting a benzene stream, a toluene stream, a xylene stream and/or any combination thereof, from the second aromatic rich stream (119) to form a raffinate stream (117) and a third aromatic rich stream (116).

Extracting as used herein refers to any process wherein at least one hydrocarbon component is isolated from a hydrocarbon stream. Extracting methods are well known within the field and by those skilled in the art and may include distillation, solvent extraction, crystallization, adsorption, azeotropic distillation and/or any combination thereof.

The raffinate stream (117) as used herein refers to an aromatically deficient hydrocarbon fraction, wherein the aromatics content by weight is less than 3%, less than 2%, less than 1%, less than 0.5% and includes a naphthene content by weight of 1-40%, preferably at least 1%, at least 10%, at least 15% at least 20%, at least 25%, at least 30%, or at least 35%. In one embodiment, the aromatic content of the raffinate stream (117) is less than 1%. In a preferred embodiment the naphthene content of the raffinate stream (117) is at least 25% and no more than 40% by weight.

The third aromatic rich stream (116) as used herein refers to a hydrocarbon stream comprising aromatic/polyaromatic hydrocarbons including benzene, toluene, xylenes, (BTX); and/or any combination thereof.

Benzene, toluene, xylenes, (BTX) and/or any combination thereof may constitute 10%-50%, preferably 15%-45%, 20%-40%, 25%-35% of the third aromatic rich stream (116) by weight.

Due to the high content of BTX within the third aromatic rich stream (116) the stream may be separated to form a benzene stream, a toluene stream, a xylenes stream and/or any combination thereof as individual aromatic products.

Alternatively, the total yield of benzene from the third aromatic rich stream (116) may be increased by dealkylating all or a portion of the third aromatic rich stream (116) in a dealkylating unit (128).

Dealkylating as used herein refers to any process where a hydrocarbon stream comprising aromatic/polyaromatic hydrocarbons in a dealkylating unit (128) is converted into lower molecular weight aromatic hydrocarbons in the presence or the absence of a converting catalyst.

A typical dealkylating process, which is well known by those skilled in the art, may include contacting an aromatic hydrocarbon stream with a conversion catalyst in the presence of hydrogen gas in a dealkylating unit (128) reaction zone at a reaction temperature range of 120° C.-600° C., a reaction pressure of 14.0-142 psig and a reaction time of 0.1-24 hours with the aromatic $C_7$-$C_8$ components and produce a dealkylated hydrocarbon vapor stream comprising mainly lower molecular weight components such as benzene, toluene, xylenes naphthene, alkanes and/or any combination thereof and condensing the dealkylated hydrocarbon vapor stream in a condensing zone and separating the condensed hydrocarbon vapor stream in a separating zone to form a benzene rich stream (129).

The conversion catalyst may comprise at least one metal selected from but not limited to group 6, 8, 9, 10, 11 metals, molybdenum, cobalt, nickel, tungsten, gold, platinum, iridium, palladium, osmium, silver, rhodium, and/or ruthenium and a support material such as a molecular sieves, alumina, and/or silica-alumina. The dealkylating may convert by weight 10%-99%, preferably at least 10%, at least 15%, at least 20%, at least 25%, at least 30%, at least 35%, at least 36%, at least 37%, at least 38%, at least 40%, at least 45%, at least 50%, at least 55%, at least 60%, at least 65%, at least 70% at least 75%, at least 80%, at least 85%, at least 90%, at least 95%, or at least 98% of the $C_9/C_{10+}$ aromatic/polyaromatic hydrocarbons are converted into lower molecular weight aromatic hydrocarbons such as BTX.

Conversion catalyst compositions, catalyst conversion rates, as well as, alternative hydrocarbon feedstock components and compositions are well known by those skilled in the art.

A typical dealkylating unit (128) comprises at least one conversion reactor including at least one reaction zone, at least one gas inlet, at least one hydrocarbon stream inlet a hydrocarbon vapor stream outlet fluidly connected to a condensing zone, fluidly connected to a separating zone.

Components such as toluene, xylenes, ethylbenzenes and other alkyl-aromatics are converted to benzene via a dealkylation process, wherein a concentration of benzene in the benzene rich stream (129) may go up to 40%, or preferably up to 50%, or preferably up to 60%, or preferably up to 70%, or preferably up to 80%, or preferably up to 90%, or preferably up to 95% by weight.

Hydrocarbon streams with a significant content of paraffins, naphthenes, or both are known by those of ordinary skill in the art to produce olefins when subjected to steam cracking. In order to increase the yield of olefins, a number of hydrocarbon streams produced during the process may be subjected to steam cracking in order to meet olefinic product demands. In one embodiment, the process further comprises steam cracking the raffinate stream (117) to form a first olefin stream. In one embodiment, the process optionally comprises steam cracking the isomerized stream (113) to further produce an olefin-rich stream in addition to the first olefin stream.

Significant content as used herein refers to a weight percent value for a component within a hydrocarbon stream that is by weight 15%-90%, preferably at least 15%, at least 20%, at least 25%, at least 30%, at least 35%, at least 40%, at least 45% at least 50%, at least 55%, at least 60%, at least 65%, at least 70%, at least 75%, at least 80%, or at least 85%.

Steam cracking the isomerized stream (113) refers to a process where the isomerized stream (113) is transported from the isomerization unit (105) to the steam cracking via a fluid connection and cracked together as a mixture with the hydrocarbon feedstock (122). Subsequently, at least 30%, at least 35%, at least 40%, at least 45%, at least 50%, at least 55%, at least 60%, at least 65%, at least 70%, at least 75%, at least 80%, at least 85%, or at least 90% preferably 30-90% by weight of the paraffinic content of the isomerized stream (113) may be converted to in the steam cracking unit (102) to form a first olefin stream (127). In one embodiment, at least 40% of the isomerized stream's (113) paraffinic content is converted to olefins.

Alternatively, steam cracking the isomerized stream (113) may include a process where the isomerized stream (113) is transported from the isomerizing unit (105) to the steam cracking unit (102) via a fluid connection as a single batch with no additional hydrocarbon feedstocks. Subsequently at least 30%, at least 35%, at least 40%, at least 45%, at least 50%, at least 55%, at least 60%, at least 65%, at least 70%, at least 75%, at least 80%, at least 85%, or at least 90% of the paraffinic content of the isomerized stream (113) may be converted to olefins during the steam cracking. In one embodiment, at least 40% of the isomerized stream's (113) paraffin content is converted to olefins.

Steam cracking the raffinate stream (117) also refers to a process where the raffinate stream (117) is transported from the extracting unit (106) to the steam cracking unit (102) via a fluid connection. Subsequently, at least 30%, at least 35%, at least 40%, at least 45%, at least 50%, at least 55%, at least 60%, at least 65%, or at least 70%, preferably 30-70% by weight of the naphthene content of the raffinate stream (117) may be converted in the steam cracking unit (102) with the second hydrocarbon feedstock to form a second olefin stream (126). In one embodiment, at least 40% of the raffinate stream's (117) naphthene content is converted to olefins.

The second olefin stream (126) as used herein refers to a hydrocarbon stream comprising by weight 30%-55%, preferably 35%-50%, or 40%-45% ethylene, 1%-30%, preferably 5%-25%, 10%-20% or 15% propylene, and 1-15%, preferably 3%-12%, or 5-9% butadiene.

According to a second aspect, the present disclosure relates to an integrated process for increasing olefin production from a combined feedstock stream comprising a pyrolysis gasoline stream (108) and a full range cracked naphtha stream (109). The process involves saturating a first aromatic rich stream (114) in a saturating unit (201) to produce a first naphthene stream (202).

Saturating as used herein refers to any process where an aromatic and/or polyaromatic-rich hydrocarbon stream is reacted in the presence of hydrogen gas (203) and a saturating catalyst to reduce carbon-carbon double bonds, resulting in the conversion of aromatic components, polyaromatic components and/or any combination thereof within a hydroprocessed, aromatically rich hydrocarbon stream and/or mixture into naphthenes.

Of particular interest is the inclusion of a saturation unit (201) for a refinery process. Conventionally, aromatic saturation is not utilized to a significant degree when refining hydrocarbon products derived from mineral oil. However, in embodiments of the invention saturation is used as a technique for increasing olefin formation. In this regard, the total amount of aromatic component(s) separated or isolated from the feed streams treated in this embodiment of the invention is substantially lower than the amount of aromatic components that are input into the process. For example, based on the total weight of aromatic components that are used as feed stream to the steam cracking unit (102), the aromatic components are reduced by an amount of 50-99.5%, preferably 60-99.5%, 70-99.5%, 80-99%, 85-95% or about 90% by weight in comparison to the total amount of aromatic components added to the process as new hydrocarbon feedstock.

A saturating unit (201) may include at least one saturating reactor including a mixing zone and a reaction zone, wherein the reaction zone comprises single and/or multiple layers/beds of a saturating catalyst, with at least one quenching zone separating multiple layers/beds in the reaction zone, and at least one hydrogen gas inlet along with at least two saturation unit stream inlets.

An exemplary saturating operation may include combining at least one aromatic- and/or polyaromatic-rich hydrocarbon stream with a hydrogen gas flow in the mixing zone to form a saturating mixture, contacting the saturating mixture with at least one layer/bed of a saturating catalyst at a saturating temperature in the range of 200° C.-400° C. and a saturating pressure range of 400 psig-1500 psig, and quenching the saturating mixture to form the first naphthene stream.

The saturating catalyst may comprise at least one metal attached to a support material. Exemplary metals may include group 6, 8, 9, 10, 11 metals, molybdenum, cobalt, nickel, tungsten, gold, platinum, iridium, palladium, osmium, silver, rhodium, and ruthenium. The support material may be selected from materials such as a molecular sieves, alumina, and silica-alumina. In an alternative embodiment, the saturating comprises reacting the first aromatic rich stream (114) with hydrogen gas in the presence of a noble metal catalyst. The saturating may convert by weight 10%-99%, preferably at least 10%, at least 15%, at least 20%, at least 25%, at least 30%, at least 35%, at least 36%, at least 37%, at least 38%, at least 40%, at least 45%, at least 50%, at least 55%, at least 60%, at least 65%, at least 70% at least 75%, at least 80%, at least 85%, at least 90%, at least 95%, or at least 98% of the aromatic components, the polyaromatic components or any combination thereof into naphthenes. In one embodiment, the saturating converts at least 90% of the aromatic rings in the first aromatic rich stream (114) into naphthenes.

In one embodiment, prior to the saturating the first aromatic rich stream (114) is processed to hydrogenate one or more dicyclopentadiene compounds present therein.

Dicyclopentadiene, (DCP) a low boiling non-aromatic cyclic hydrocarbon which may be found within the pyrolysis gasoline stream (108), the full range cracked naphtha stream (109), and/or any combination thereof may deactivate the saturating catalyst, e.g., by polymerizing during the saturating. To reduce the likelihood of DCP polymerizing, processing the pyrolysis gasoline stream (108), the full range cracked naphtha stream (109), the hydro-processed combined stream (111), the first aromatic rich stream (114) and/or any combination thereof to remove DCP prior to the saturating may be advantageous. Exemplary processing procedures could include crystal fractionalization, hydrogenation (i.e. saturation), and distillation. In one embodiment, prior to the saturating the first aromatic rich stream (114) is processed to saturate one or more dicyclopentadiene compounds present therein producing a DCP-deficient first aromatic rich stream, wherein in the DCP is less than 1.0%, preferably less than 0.5%, more preferably less than 0.1% by weight relative to the first aromatic rich stream (114) which contains the DCP.

The saturating may convert 10%-99% by weight, preferably at least 10%, at least 15%, at least 20%, at least 25%, at least 30%, at least 40%, at least 50%, at least 60%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% of the aromatic components, the polyaromatic components or any combination thereof into naphthenes. In one embodiment, the saturating converts at least 90% of the aromatic rings in the second aromatic rich stream (119) into naphthenes.

The first naphthene stream (202) as used herein refers to an output hydrocarbon stream from saturating the second aromatic rich stream (119). The first naphthene stream's (202) naphthene content may be higher than the second aromatic rich stream (119). In one embodiment, the first naphthene stream (202) comprises a naphthene content of at least 60%, at least 70%, at least 80%, at least 90%, at least 99.9% by weight of the first naphthene stream (202).

Hydrocarbon streams with a significant content of paraffins, naphthenes, and/or both are known by those of ordinary skill in the art to produce olefins when subjected to steam cracking. In order to increase the yield of olefins from the disclosed invention, a number of hydrocarbon streams produced during the process may be subjected to steam cracking in order to meet olefinic product demands. In one embodiment, the process further comprises steam cracking the first naphthene stream (202) to form a first olefin stream. In one embodiment the process further comprises steam cracking the isomerized stream (113) to produce a first olefin stream (126).

Steam cracking the first naphthene stream (202) refers to a process where the first naphthene stream (202) is transported downstream from the saturating unit to the steam cracking unit (102) via a fluid connection. Subsequently at least 30%, at least 35%, at least 40%, at least 45%, at least 50%, at least 55%, at least 60%, at least 65%, at least 70%, preferably 30-70% by weight of the naphthene content of the first naphthene stream (202) may be converted to olefins in the steam cracking unit (102).

According to a third aspect, the present disclosure relates to an integrated process for increasing olefin and aromatic production using a combined feedstock stream comprising a pyrolysis gasoline stream (108) and a full range cracked naphtha stream (109). The process involves saturating at least a portion of the first aromatic rich stream (114), the heavy oil stream (115), light pyrolysis oil stream (130), in the saturating unit (201) to form a second naphthene stream (301), extracting a second aromatic rich stream (116) in the extraction unit (106) from at least a portion of the first aromatic rich stream (114) to form the raffinate stream (117), steam cracking, the isomerized/non-isomerized stream (113), the raffinate stream (117), the second naphthene stream (301), and/or any combination thereof in the steam cracking unit (102) to produce the first olefin stream and the second olefin stream, while optionally dealkylating the second aromatic rich stream (116) in a dealkylation unit (128) to form the benzene rich stream (129), which is rich in benzene content.

Dividing the aromatically rich second aromatic rich stream (119) derived from the previously described combined feedstock stream (110) provides an aromatically rich feedstock for producing olefins as well as an aromatic product stream. This allows a modern refinery to service the demand for olefin and aromatic products and can be adjusted for the relative need for each product by changing the volume ratio of the second aromatic rich stream (119) sent to the extraction unit (106) and the saturation unit (201) by splitting (107). The volume ratio of the total first aromatic rich stream sent to the extraction unit (106) vs the saturating unit may include a range of 1:10 to 10:1, preferably 1:9 to 9:1, 1:8 to 8:1, 1:7 to 7:1, 1:6 to 6:1, 1:5 to 5:1, 1:4 to 4:1, 1:3 to 3:1, 1:2 to 2:1 or 1:1.

The second naphthene stream (301) as used herein refers to an output hydrocarbon stream from the saturating unit (201) formed by saturating at least a portion of the second aromatic rich stream (119), and optionally at least a portion of the heavy oil stream (115). In one embodiment the second naphthene stream (301) comprises a naphthene content of 60-99% by weight, preferably at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% by weight.

The volume ratio of the second aromatic rich stream (119) to the heavy oil stream sent to the saturating unit (201) or vice versa may include a range of 1:10 to 10:1, preferably 1:9 to 9:1, 1:8 to 8:1, 1:7 to 7:1, 1:6 to 6:1, 1:5 to 5:1, 1:4 to 4:1, 1:3 to 3:1, 1:2 to 2:1 or 1:1.

The second naphthene stream (301), the isomerized stream (113), the raffinate stream (117) and/or any combination thereof may by weight increase 1%-60%, preferably at least 1%, at least 5%, at least 10%, at least 15%, at least 16%, at least 17%, at least 18%, at least 19%, at least 20%, at least 25%, at least 30%, at least 35%, at least 40%, at least 50%, or at least 60% by weight the total olefin production when compared to non-integrated processes not using a combined feedstock stream as shown in FIG. 4, and FIG. 5.

It can be envisioned where in any disclosed embodiment, the isomerized stream, the first naphthene stream, the second naphthene stream, the raffinate stream, and/or any combination thereof is passed to a separate integrated steam cracking unit to produce the respective olefin streams individually, as a single hydrocarbon stream/mixture rich in olefins, and/or as a component of a steam cracked hydrocarbon mixture.

The invention claimed is:

1. An integrated process for forming a combined feedstock stream comprising a pyrolysis gasoline stream and a full range cracked naphtha stream to produce a plurality of olefin streams and a plurality of aromatic hydrocarbon streams, comprising:
   catalytically cracking a first hydrocarbon feedstock and separating the catalytically cracked first hydrocarbon feedstock to form a full range cracked naphtha stream and a first light olefins stream wherein the first light olefins stream comprises ethylene, propylene, butadiene and/or any combination thereof;
   steam cracking a second hydrocarbon feedstock and separating the steam cracked second hydrocarbon feedstock to form a heavy pyrolysis oil stream, a pyrolysis gasoline stream and a second light olefins stream wherein the second light olefins stream comprises ethylene, propylene, butadiene and/or any combination thereof;
   mixing at least a portion of the full range cracked naphtha stream and at least a portion of the pyrolysis gasoline stream to form a combined stream;
   hydro-processing the combined stream and separating the hydro-processed effluent stream to form a hydro-processed combined stream and a light pyrolysis oil stream;
   splitting the hydro-processed combined stream into:
      a $C_5/C_6$ stream; and
      a first aromatic rich stream comprising aromatic $C_6$ molecules, aromatic $C_7$ molecules, aromatic $C_8$ molecules, aromatic $C_9$ molecules and/or any combination thereof; and
   splitting the first aromatic rich stream into:
      a second aromatic rich stream; and
      a heavy oil stream.

2. The process of claim 1, wherein the hydro-processing comprises:
   hydrogenating the combined stream with a first hydro-processing catalyst to convert one or more diolefins present in the combined stream into one or more mono-olefin to yield a hydrogenated combined streams;
   saturating the hydrogenated combined stream with a second hydro-processing catalyst to convert mono-olefins into paraffins; and
   removing one or more components comprising nitrogen, sulfur, metals and/or any combination thereof from the combined stream to form the hydro-processed combined stream.

3. The process of claim 1, wherein the full range cracked naphtha stream comprises by weight:
   5%-40% mono-olefins;
   10%-20% paraffins; and
   30%-45% aromatics/polyaromatics.

4. The process of claim 1, wherein the pyrolysis gasoline stream comprises by weight:
   5%-10% mono-olefins;
   10%-20% paraffins;
   15%-25% diolefins; and
   30%-55% aromatics/polyaromatics.

5. The process of claim 1, wherein the combined stream comprises by weight:
   10%-20% mono-olefins;
   10%-20% paraffins;
   15%-20% diolefins; and
   35%-50% aromatics/polyaromatics.

6. The process of claim 1, further comprising:
   isomerizing the $C_5/C_6$ stream to form an isomerized stream.

7. The process of claim 1, further comprising:
   extracting benzene, toluene, xylenes, and/or any combination thereof, from the second aromatic rich stream to form a raffinate stream and a third aromatic rich stream.

* * * * *